US012612352B2

(12) United States Patent
Knopff

(10) Patent No.: US 12,612,352 B2
(45) Date of Patent: Apr. 28, 2026

(54) PROCESS FOR PREPARING PERFUMING INTERMEDIATE

(71) Applicant: Firmenich SA, Satigny (CH)

(72) Inventor: Oliver Knopff, Satigny (CH)

(73) Assignee: Firmenich SA, Satigny (CH)

( * ) Notice: Subject to any disclaimer, the term of this patent is extended or adjusted under 35 U.S.C. 154(b) by 850 days.

(21) Appl. No.: 17/793,216

(22) PCT Filed: Mar. 4, 2021

(86) PCT No.: PCT/EP2021/055498

§ 371 (c)(1),
(2) Date: Jul. 15, 2022

(87) PCT Pub. No.: WO2021/176009

PCT Pub. Date: Sep. 10, 2021

(65) Prior Publication Data

US 2023/0095887 A1 Mar. 30, 2023

(30) Foreign Application Priority Data

Mar. 5, 2020 (EP) ..................................... 20161118

(51) Int. Cl.

| | |
|---|---|
| ***C07C 45/68*** | (2006.01) |
| ***B01J 31/22*** | (2006.01) |
| ***C07C 45/67*** | (2006.01) |
| ***C07C 49/687*** | (2006.01) |

(52) U.S. Cl.

CPC ........... *C07C 45/68* (2013.01); *B01J 31/2295* (2013.01); *C07C 45/673* (2013.01); *C07C 49/687* (2013.01); *C07C 2601/08* (2017.05)

(58) Field of Classification Search

None

See application file for complete search history.

(56) References Cited

FOREIGN PATENT DOCUMENTS

JP S5444640 A 4/1979

OTHER PUBLICATIONS

Bandini, M. "A Cross Metathesis Based Protocol for the Effective Synthesis of Functionalised Allyl Bromides and Chlorides" Synthesis 2004, No. 3, pp. 0409-0414 (Year: 2004).*

LifeChemicals "2-(Prop-2-en-1-yl)cyclopentan-1-one", Deposit and available date Oct. 29, 2017 (Year: 2017).*

Emura, C. et al. "Synthetic Studies on the Natural Multidrug Resistance Modulator, Irciniasulfonic Acid B" Chem. Lett. 2010, 39, 1002-1003 (Year: 2010).*

Shakhmaev, R. N. et al. "Iron-Catalyzed Synthesis of 2-[(2E)-Hex-2-en-1-yl]cyclopentanone" Russian Journal of Organic Chemistry, 2018, vol. 54, No. 3, pp. 500-502 (Year: 2018).*

Bahurel et al., "A new Method for Conversion of cis-Vinyl Spiranic Ketones to the Corresponding cis-Dienones", Synthesis, 1974, pp. 118-119, 1974(2).

Hughes, Gregory et al., The use of 1,4-dichlorobut-2-ene as a synthetic equivalent of 4-bromobut-1-ene, Synlett , 6: 835-837 (2000).

Robertson J et al., Radical Cascade Processes Leading to Fused- and Spiro-Bicyclic Ring Systems, Tetrahedron, 56(45):8959-8965 (2000).

Naf et al., An Efficient Synthesis of Methyl-Jasmonate and (Z)-Jasmone, Helvetica Chimica Acta, 61(7):2524-2529 (2000).

Tsuda, Tetsuo et al., Palladium-catalyzed reaction of 1,3-diene monoepoxides with beta-keto acids. Allylic alkylation and isomerization of 1,3-diene monoepoxides. Journal of Organic Chemistry, 51(26):5216-21, (1986).

* cited by examiner

*Primary Examiner* — Medhanit W Bahta

(74) *Attorney, Agent, or Firm* — Armstrong Teasdale LLP

(57) ABSTRACT

The present invention relates to the field of organic synthesis and more specifically it concerns a process for preparing compound of formula (I) by a cross metathesis reaction. Said compound of formula (I) is valuable new chemical intermediate for producing perfuming ingredients and is also part of the present invention.

14 Claims, No Drawings

PROCESS FOR PREPARING PERFUMING INTERMEDIATE

This present application is a U.S. national phase entry under 35 U.S.C. § 371 of PCT Application No. PCT/EP2021/055498, filed Mar. 4, 2021, which claims priority to European Patent Application No. 20161118.3, filed Mar. 5, 2020. The entire contents of these applications are explicitly incorporated herein by this reference.

TECHNICAL FIELD

The present invention relates to the field of organic synthesis and more specifically it concerns a process for preparing compound of formula (I) by a cross metathesis reaction. Said compound of formula (I) is valuable new chemical intermediate for producing perfuming ingredients and is also part of the present invention.

BACKGROUND

Some of the most sought ingredients in the perfumery field are the ones imparting a floral impression. In this odor family, Methyl jasmonate and cis jasmone represent key natural occurring perfuming ingredients imparting an odor reminiscent of the floral heart of jasmin. One of the valuable intermediate to prepare them is (Z)-2-(pent-2-en-1-yl)cyclopent-2-en-1-one. However, the presence of a double bond in a Z configuration complicates the access to those compounds which have been generally obtained through a Wittig reaction or the selective hydrogenation of the corresponding triple bond. Most of the reported access to (Z)-2-(pent-2-en-1-yl)cyclopent-2-en-1-one use expensive starting materials, expensive conditions such as Wittig conditions and may request supplementary protection/deprotection steps.

In *Helvetica Chimica Acta,* 1978, 2524, (Z)-2-(pent-2-en-1-yl)cyclopent-2-en-1-one is obtained via the addition of 1,4-dibromo-2-pentene on cyclopentanone providing a spiro compounds followed by a [1,5]hydrogen shift. However, the preparation of 1,4-dibromo-2-pentene requires the use of highly toxic bromine.

So there is still a need to develop a cheaper and more straightforward approach towards (Z)-2-(pent-2-en-1-yl)cyclopent-2-en-1-one.

The present invention allows obtaining compound of formula (I), which may be easily converted into (Z)-2-(pent-2-en-1-yl)cyclopent-2-en-1-one via basic treatment and thermolysis, by cross metathesis between commercially available or easily available compounds of formula (II) and (III).

SUMMARY OF THE INVENTION

The invention relates to a novel process allowing the preparation of compound of formula (I) starting from compound of formula (II) and (III) while avoiding the use of any toxic reagent.

So, a first object of the present invention is a process for the preparation of a compound of formula (I)

(I)

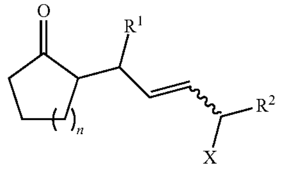

in the form of any one of its stereoisomers or a mixture thereof, and wherein n is an integer between 1 and 4; $R^1$ and $R^2$, independently from each other, represent a hydrogen atom or a $C_{1-3}$ alkyl group; and X represents a halogen atom or a OR' group wherein R' represents a hydrogen atom, a $C_{1-6}$ alkyl group, a $C_{2-6}$ alkenyl group, a benzyl group, a trimethylsilyl group, a tetrahydrofuran-2-yl group, a tetrahydro-2H-pyran-2-yl group, a $CO(O)_mR''$ group, a $CH_2(OR''')$ group, a $CH(OR''')CH_3$ group or a $SO_2R''''$ group wherein m is 0 or 1, R'' represents a hydrogen atom, a $C_{1-6}$ alkyl group or a phenyl group, R''' represents a $C_{1-6}$ alkyl group and R'''' represents a methyl, a trifluoromethyl, a phenyl or a tolyl group;

by cross metathesis between compound of the formulae (II)

(II)

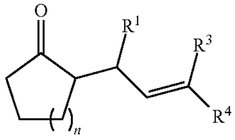

in the form of any one of its stereoisomers or a mixture thereof, and wherein n and $R^1$ have the same meaning as defined in formula (I) and $R^3$ and $R^4$, independently from each other, represent a hydrogen atom or a $C_{1-6}$ alkyl group optionally substituted by an oxo group;

with compound of formula (III)

(III)

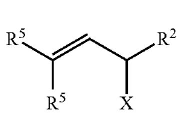

in the form of any one of its stereoisomers or a mixture thereof, and wherein X and $R^2$ have the same meaning as defined in formula (I) and $R^5$, independently from each other, represent a hydrogen atom or a $C_{1-5}$ alkyl group optionally substituted by a X group as defined above, in particular, optionally substituted by a halogen atom;

in the presence of a metathesis catalyst.

A second object of the present invention is a compound of formula (I)

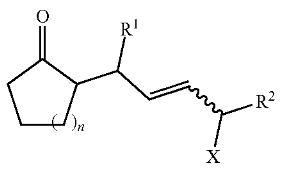

in the form of any one of its stereoisomers or a mixture thereof, and wherein n is an integer between 1 and 4; $R^1$ and $R^2$, independently from each other, represent a hydrogen atom or a $C_{1-3}$ alkyl group; and X represents a halogen atom or a OR' group wherein R' represents a hydrogen atom, a $C_{1-6}$ alkyl group, a $C_{2-6}$ alkenyl group, a benzyl group, a trimethylsilyl group, a tetrahydrofuran-2-yl group, a tetrahydro-2H-pyran-2-yl group, a $CO(O)_mR''$ group, a $CH_2(OR''')$ group, a $CH(OR''')CH_3$ group or a $SO_2R''''$ group wherein m is 0 or 1, R'' represents a hydrogen atom, a $C_{1-6}$ alkyl group or a phenyl group, R''' represents a $C_{1-6}$ alkyl group and R'''' represents a methyl, a trifluoromethyl, a phenyl or a tolyl group.

DESCRIPTION OF THE INVENTION

Surprisingly, it has now been discovered that (Z)-2-(pent-2-en-1-yl)cyclopent en-1-one, key building block toward perfuming ingredients, can be produced in an advantageous manner by means of a cross metathesis reaction between compound of formula (II) and compound of formula (III) followed by basic treatment and followed by a [1,5]hydrogen shift. The invention's conditions allow a straightforward access to (Z)-2-(pent-2-en-1-yl)cyclopent-2-en-1-one with high selectivity toward the Z stereochemistry.

Therefore, a first object of the present invention is a process for the preparation of a compound of formula (I)

(I)

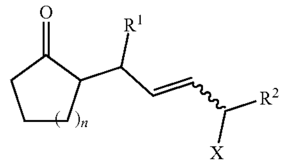

in the form of any one of its stereoisomers or a mixture thereof, and wherein n is an integer between 1 and 4; $R^1$ and $R^2$, independently from each other, represent a hydrogen atom or a $C_{1-3}$ alkyl group; and X represents a halogen atom or a OR' group wherein R' represents a hydrogen atom, a $C_{1-6}$ alkyl group, a $C_{2-6}$ alkenyl group, a benzyl group, a trimethylsilyl group, a tetrahydrofuran-2-yl group, a tetrahydro-2H-pyran-2-yl group, a $CO(O)_mR''$ group, a $CH_2(OR''')$ group, a $CH(OR''')CH_3$ group or a $SO_2R'''$ group wherein m is 0 or 1, R'' represents a hydrogen atom, a $C_1$-6 alkyl group or a phenyl group, R''' represents a $C_{1-6}$ alkyl group and R''' represents a methyl, a trifluoromethyl, a phenyl or a tolyl group;

by cross metathesis between compound of the formulae (II)

(II)

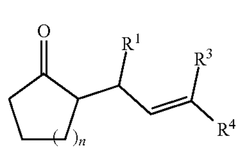

in the form of any one of its stereoisomers or a mixture thereof, and wherein n and $R^1$ have the same meaning as defined in formula (I) and $R^3$ and $R^4$, independently from each other, represent a hydrogen atom or a $C_{1-6}$ alkyl group optionally substituted by an oxo group;

with compound of formula (III)

(III)

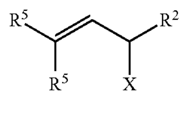

in the form of any one of its stereoisomers or a mixture thereof, and wherein X and $R^2$ have the same meaning as defined in formula (I) and $R^5$, independently from each other, represent a hydrogen atom or a $C_{1-6}$ alkyl group optionally substituted by a X group as defined above, in particular, optionally substituted by a halogen atom;

in the presence of a metathesis catalyst.

For the sake of clarity, by the wavy bond in compound of formula (I), or the similar, it is meant the normal meaning understood by a person skilled in the art, i.e. that the double bond may have a cis configuration, a trans configuration or a mixture thereof.

The term "optionally" is understood that a certain group to be optionally substituted can or cannot be substituted with a certain functional group.

The terms "alkyl" and "alkenyl" are understood as comprising cyclic, branched and linear alkyl and alkenyl groups, preferably a linear alkyl and alkenyl groups. The terms "alkenyl" is understood as comprising 1, 2 or 3 olefinic double bonds, preferably 1 olefinic double bonds.

The term "oxo group" are understood as comprising any group of formula =O; i.e. such as a ketone or an aldehyde. In other words, a $C_{1-6}$ alkyl group optionally substituted an oxo group is an alkyl group having from 1 to 6 carbons and one of these carbon atoms, even the terminal carbon, may be substituted by a =O group instead of two hydrogen atoms.

According to any embodiments of the invention, and independently of the specific aspects, the compound (I) as well as the corresponding compound (II) and (III) can be in the form of any one of its stereoisomers or mixture thereof.

For the sake of clarity by the term stereoisomer it is intended any diastereoisomer, enantiomer, racemate.

Indeed, the compound (I), (II) or (III) may have at least one stereogenic center which can have different stereochemistry (i.e. when two stereogenic centers are present, compound (I), (II) or (III) can have (R,R), (S,S), (S,R) or (R,S) configuration). Each of said stereogenic centers can be in a relative configuration R or S or a mixture thereof or in other words said compound of formula (I), (II) or (III) can be in a form of pure enantiomer or diastereoisomer, or in a form of a mixture of stereoisomers. In addition, said compound of formula (I), (II) or (III) can be in the form of its E or Z isomer or of a mixture thereof, e.g. the invention comprises compositions of matter consisting of one or more compounds of formula (I), (II) or (III), having the same chemical structure but differing by the configuration of the double bond.

According to any one of the above embodiments of the invention, said compounds of formula (I) are $C_9$-$C_{15}$ compounds.

According to any embodiments of the invention, n may be 1 or 2. In particular, n may be 1.

According to any embodiments of the invention, $R^1$ may be a hydrogen atom or a methyl group, in particular a hydrogen atom.

According to any embodiments of the invention, $R^2$ may represent a $C_{1-3}$ alkyl group. In particular, $R^2$ may represent a methyl or an ethyl group. Even more particularly, $R^2$ may represent a methyl group.

According to any embodiments of the invention, X may be a halogen atom or a OR' group wherein R' represents a $C_{1-6}$ alkyl group, a $C_{2-6}$ alkenyl group, a trimethylsilyl group, a $CO(O)_mR''$ group, a $CH(OR''')CH_3$ group or a $SO_2R'''$ group wherein m is 0 or 1, R'' represents a $C_{1-6}$ alkyl group, R''' represents a $C_{1-6}$ alkyl group and R''' represents a methyl, a trifluoromethyl, a phenyl or a tolyl group.

Particularly, X may be a halogen atom, a OR' group wherein R' represents a hydrogen atom, a $C_{1-6}$ alkyl group, a $C_{2-6}$ alkenyl group, an acetyl group, a methoxymethyl group, a ethoxymethyl group, 1-butoxyethyl group, a 1-ethoxyethyl group, a trimethylsilyl group, a methanesulfonyl group, a benzenesulfonyl group or a toluenesulfonyl group. Particularly, X may be a halogen atom, a OR' group wherein R' represents a $C_{1-6}$ alkyl group, a $C_{2-6}$ alkenyl group, an acetyl group, a methanesulfonyl group, a benzensulfonyl group or a toluenesulfonyl group. Particularly, X may be a halogen atom, a OR' group wherein R' represents a hydrogen atom, an acetyl group, a methoxymethyl group, a ethoxymethyl group, 1-butoxyethyl group, a 1-ethoxyethyl group or a trimethylsilyl group. Particularly, X may be a halogen atom, a OR' group wherein R' represents a $C_{1-6}$ alkyl group, a methanesulfonyl group, benzenesulfonyl or a toluenesulfonyl group. Particularly, X may be a halogen atom. Even more particularly, X may be a chloride atom.

According to any embodiments of the invention, $R^3$ may represent a hydrogen atom or a $C_{1-3}$ alkyl group. Particularly, $R^3$ may represent a hydrogen atom or a methyl group. Even more particularly, $R^3$ may represent a hydrogen atom.

According to any embodiments of the invention, $R^4$ may represent a hydrogen atom, a $C_{1-3}$ alkyl group or a (2-oxocyclopentyl)methyl group. Particularly, $R^4$ may represent a hydrogen atom, a methyl group or an ethyl group. Even more particularly, $R^4$ may represent a hydrogen atom.

According to any embodiments of the invention, $R^5$, independently from each other, may represent a hydrogen atom, a $C_{1-3}$ alkyl group optionally substituted by a halogen atom or a OR' group wherein R' represents a trimethylsilyl group, COR" group, a $CH_2(OR''')$ group or a $CH(OR''')CH_3$ group wherein R" represents a hydrogen atom, a $C_{1-6}$ alkyl group or a phenyl group, R''' represents a $C_{1-6}$ alkyl group. Particularly, one $R^5$ may be a hydrogen atom and the other $R^5$ may be a hydrogen atom, a $C_{1-3}$ alkyl group optionally substituted by a halogen atom or a OR' group wherein R' represents a trimethylsilyl group, COR" group, a $CH_2(OR''')$ group or a $CH(OR''')CH_3$ group R" represents a hydrogen atom, a $C_{1-6}$ alkyl group or a phenyl group, R''' represents a $C_{1-6}$ alkyl group. Particularly, one $R^5$ may be a hydrogen atom and the other $R^5$ may represent a hydrogen atom, a $C_{1-3}$ alkyl group optionally substituted by a halogen atom. Particularly, one $R^5$ may be a hydrogen atom and the other $R^5$ may represent a hydrogen atom, a $C_{1-2}$ alkyl group optionally substituted by a chloride atom. Even more particularly, one $R^5$ may be a hydrogen atom and the other $R^5$ may represent a hydrogen atom, an ethyl group or an 1-chloroethyl group. Even more particularly, $R^5$ may represent a hydrogen atom.

According to any embodiments of the invention, R' may represent a $C_{1-3}$ alkyl group, particularly, a methyl or an ethyl group.

According to any embodiments of the invention, R" may represent a phenyl group or a $C_{1-3}$ alkyl group, particularly, a methyl or an ethyl group.

According to any embodiments of the invention, R''' may represent a $C_{1-4}$ alkyl group, particularly, a $C_{1-3}$ alkyl group, even more particularly, a methyl or an ethyl group.

Non-limiting examples of suitable compounds of formula (I) may include 2-(4-chloropent-2-en-1-yl)cyclopentan-1-one, 5-(2-oxocyclopentyl)pent-3-en-2-yl acetate, 5-(2-oxocyclopentyl)pent-3-en-2-yl methanesulfonate, 2-(4-bromopent-2-en-1-yl)cyclopentan-1-one, 2-(4-(1-butoxyethoxy)pent-2-en-1-yl)cyclopentan-1-one, 2-(4-(1-ethoxyethoxy)pent-2-en-1-yl)cyclopentan-1-one, 2-(4-((tetrahydro-2H-pyran-2-yl)oxy)pent-2-en-1-yl)cyclopentan-1-one, 2-(4-((tetrahydrofuran-2-yl)oxy)pent-2-en-1-yl)cyclopentan-1-one or 2-(4-((trimethylsilyl)oxy)pent-2-en-1-yl)cyclopentan-1-one.

Non-limiting examples of suitable compounds of formula (II) may include 2-(3-methylbut-2-en-1-yl)cyclopentan-1-one, 2-(pent-2-en-1-yl)cyclopentan-1-one, 2,2'-(but-2-ene-1,4-diyl)bis(cyclopentan-1-one), 2-allylcyclopentan-1-one, 2-(hex-2-en-1-yl)cyclopentan-1-one or 2-(oct-2-enyl)cyclopentan-1-one.

Non-limiting examples of suitable compounds of formula (III) may include 2-chlorohex-3-ene, 2-chloropent-3-ene, 2,5-dichlorohex-3-ene, but-3-en-2-yl acetate, hex-3-ene-2,5-diyl diacetate, 2-bromohex-3-ene, 4-chloropent-2-ene, 4-bromopent-2-ene, 3-chlorobut-1-ene, 3-bromobut-1-ene, 3-(1-butoxyethoxy)but-1-ene, 3-(1-ethoxyethoxy)but-1-ene, 2-(but-3-en-2-yloxy)tetrahydrofuran, 2-(but-3-en-2-yloxy)tetrahydro-2H-pyran, (but-3-en-2-yloxy)trimethylsilane, but-3-en-2-ol or hex-3-ene-2,5-diol.

The compounds of formula (II) and (III) are commercially available compounds or can be prepared by several methods, such as the one reported in J. K. Crandall, H. S. Magaha, G. K. Widener, G. A. Tharp Tetrahedron Lett., 21 (1980), pp. 4807-4810 for compounds of formula (II) or in Kharasch, M. S. et al Journal of Organic Chemistry, 3, 409-413; 1938 for compounds of formula (III).

According to any embodiments of the invention, the metathesis catalyst may be a cross-metathesis catalyst. In particular, the metathesis catalyst may be a Ruthenium-based catalyst, Molybdenum-based catalyst, Rhenium-based catalyst or Tungsten-based catalyst. Particularly, the metathesis catalyst may be a Ruthenium-based catalyst. The Ruthenium-based metathesis catalyst may be a Ruthenium(II) carbenoid complex. The nature and type of Ruthenium-based metathesis catalyst used in the invention's process do not warrant a more detailed description here, which in any case would not be exhaustive, the skilled person being able to select them on the basis of his general knowledge. Said catalysts are in any case listed in reference texts such as Grubbs, R. H. *Handbook of Metathesis*; Wiley-VCH: New York, 2003; 1204 pages, 3 volumes, The Strem Chemiker—Vol. XXVIII No. 1, June, 2015, pages 1-24. Booklet Strem Metathesis Catalysts February 2020, R. H. Grubbs, A. G. Wenzel, D. J. OLeary, E. Khosravi, Handbook of Metathesis, Wiley-VCH, Weinheim, 2015, K. Grela, Olefin Metathesis: Theory and Practice, Wiley, Hoboken, 2014 or in other works of a similar nature, as well as in the abundant patent literature in the field of metathesis processes. Non-limiting examples of suitable metathesis catalyst may include (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II), (1,3-bis(2,6-diisopropylphenyl)imidazolidin-2-ylidene)diiodo(2-((1-(methoxy(methyl)amino)-1-oxopropan-2-yl)oxy)benzylidene)ruthenium(II), (1,3-dimesitylimidazolidin-2-ylidene)dichloro(2-isopropoxy-5-nitrobenzylidene)ruthenium(II), Dichloro[1,3-bis(2,4,6-trimethylphenyl)-2-imidazolidinylidene](2-isopropoxyphenylmethylene)ruthenium(II), Benzylidene-bis(tricyclohexylphosphine)dichlororuthenium, Dichloro[1,3-bis(2,6-isopropylphenyl)-2-imidazolidinylidene](2-isopropoxyphenylmethylene)ruthenium(II), [1,3-Bis2,6-di-i-propylphenyl)imidazolidin-2-ylidene)(2-i-propoxy-5-nitrobenzylidene) ruthenium(II) diiodide, 1,3-Bis(2,6-di-i-propylphenyl)imidazolidin-2-ylidene)(2-i-propoxy-5-nitrobenzylidene) ruthenium(II) dichloride, (1,3-Dimesitylimidazolidin-2-ylidene)diiodo(2-isopropoxy-5-nitrobenzylidene)ruthenium(II), Bis(1-(2,6-diethylphenyl)-3,5,5-trimethyl-3-phenylpyrrolidin-2-ylidene)(3-phenyl- 1H-inden-1-ylidene)ruthenium(II) dichloride, (1-(2,6-diethylphenyl)-3,5,5-trimethyl-3-phenylpyrrolidin-2-ylidene)dichloro(2-isopropoxy-5-nitrobenzylidene) ruthenium(II), (1-(2,6-diethylphenyl)-3,5,5-trimethyl-3-phenylpyrrolidin-2-ylidene)diiodo(2-isopropoxy-5-nitrobenzylidene)ruthenium(II), Dichloro[1,3-bis(2,4,6-trimethylphenyl)-2-imidazolidinylidene](benzylidene) (tricyclohexylphosphine)ruthenium(II), Dichloro[1,3-bis(2-methylphenyl)-2-imidazolidinylidene](2-isopropoxyphenylmethylene)ruthenium(II), (2-(2,6-Diethylphenyl)-3,3-dimethyl-2-azaspiro[4.5]decan-1-yl)(2-isopropoxy-5-nitrobenzylidene)ruthenium(II) dichloride, [2-(1-Methylethoxy-O)phenylmethyl-C](nitrato-O,O'){rel-(2R,5R,7R)-adamantane-2,1-diyl[3-(2,4,6-trimethylphenyl)-1-imidazolidinyl-2-ylidene]}ruthenium, Dichloro(2-isopropoxyphenylmethylene) (tricyclohexylphosphine) ruthenium(II), Dichloro(3-phenyl-1H-inden-1-ylidene)bis (tricyclohexylphosphine)ruthenium(II), 1,3-Bis(2,4,6-trimethylphenyl)-4,5-dihydroimidazol-2-ylidene[2-(i-propoxy)-5-(N,N-dimethylamino sulfonyl)phenyl] methyleneruthenium(II) dichloride (resin supported), Tricyclohexylphosphine[1,3-bis(2,4,6-trimethylphenyl)imidazol-2-ylidene][3-phenyl-1H-inden-1-ylidene]ruthenium (II) dichloride, Dichloro[1,3-bis(2,4,6-trimethylphenyl) imidazolidinylidene](3-phenyl-1H-inden-1-ylidene) (tricyclohexylphosphine)ruthenium(II), [1,3-Bis(2,4,6-trimethylphenyl)-2-imidazolidinylidene]-[2-[ [(4-methylphenyl)imino]methyl]-4-nitrophenolyl]-[3-phenyl-1H-inden-1-ylidene]ruthenium(II) chloride, Dichloro[1,3-bis(2,4,6-trimethylphenyl)-2-imidazolidinylidene][[5-[(dimethylamino)sulfonyl]-2-(1-methylethoxy-O)phenyl] methylene-C]ruthenium(II), Dichloro[1,3-Bis(2-methylphenyl)-2-imidazolidinylidene](benzylidene) (tricyclohexylphosphine)ruthenium(II), Dichloro[1,3-bis(2,4,6-trimethylphenyl)-2-imidazolidinylidene](3-methyl-2-butenylidene) (tricyclohexylphosphine)ruthenium(II), Dichloro[1,3-bis(2,4,6-trimethylphenyl)-2-imidazolidinylidene](3-methyl-2-butenylidene)(dipyridine)ruthenium (II), [1,3-Bis(2,4,6-trimethylphenyl)-4-[trimethylammonio) methyl]imidazolidin-2-ylidene]-(2-i-propoxy-5-nitrobenzylidene)dichlororuthenium(II) chloride, Dichloro [1-(2,6-diisopropylphenyl)-2,2,4-trimethyl-4-phenyl-5-pyrrolidinylidene](2-isopropoxyphenylmethylene) ruthenium(II), [1,3-Bis(2,6-diisopropylphenyl)-2-imidazolidinylidene]dichloro[(2-isopropoxy)(5-trifluoroacetamido)benzylidene]ruthenium(II), Dichloro[1,3-bis(2,4,6-trimethylphenyl)-2-imidazolidinylidene](2-methoxyphenylmethylene)ruthenium(II), Dichloro[1,3-bis (2,4,6-trimethylphenyl)-2-imidazolidinylidene](3-methyl-2-butenylidene)(dipyridine)ruthenium(II), Dichloro[1,3-bis(2,4,6-trimethylphenyl)-2-imidazolidinylidene](3-phenyl-1H-inden-1-ylidene)(diphenylmethoxyphosphine)ruthenium (II), Dichloro[1,3-bis(2,4,6-trimethylphenyl)-2-imidazolidinylidene](3-phenyl-1H-inden-1-ylidene) (triphenylphosphine)ruthenium(II), Dichloro[1,3-bis(2,6-diisopropylphenyl)-2-imidazolidinylidene](benzylidene) (tricyclohexylphosphine)ruthenium(II), Dichloro[1,3-bis(2,4,6-trimethylphenyl)-2-imidazolidinylidene](3-phenyl-1H-inden-1-ylidene)diphenylphenoxyphosphine]ruthenium(II), Dichloro[1,3-bis(2-isopropylphenyl)-2-imidazolidinylidene](2-isopropoxyphenylmethylene)ruthenium(II), Dichloro[1-(2,4,6-trimethylphenyl)-2,2,4-trimethyl-4-phenyl-5-pyrrolidinylidene](2-isopropoxyphenylmethylene)ruthenium(II), Dichloro[1-(2,6-diisopropylphenyl)-2,2,4-trimethyl-4-phenyl-5-pyrrolidinylidene](2-isopropoxyphenylmethylene)ruthenium(II), Dichloro(3-methyl-2-butenylidene)bis(tricyclohexylphosphine) ruthenium(II), Dichloro[1,3-bis(2,4,6-trimethylphenyl)-2-imidazolidinylidene][2-(N,N-dimethylamino)-phenylmethylene]ruthenium(II), Dichloro[1,3-bis(2,6-diisopropylphenyl) imidazolidinylidene][2-(N,N-dimethylamino)-phenylmethylene]ruthenium(II), Dichloro [1,3-bis(2,4,6-trimethylphenyl)-2-imidazolidinylidene] (benzylidene)(tri-nbutylphosphine) ruthenium(II), Dichlorobis[1,3-bis(2,4,6-trimethylphenyl)-2-imidazolidinylidene](benzylidene)ruthenium(II), Dichlorobis[1,3-bis (2,4,6-trimethylphenyl)-2-imidazolidinylidene](2-isopropoxyphenylmethylene)ruthenium(II), (1,3-di-o-tolylimidazolidin-2-ylidene)dichloro(2-isopropoxy-5-nitrobenzylidene)ruthenium(II), Dichloro(2-isopropoxy-5-nitrophenylmethylene)(tricyclohexylphosphine)ruthenium (II), 1,3-Bis(2,4,6-trimethylphenylimidazolidin-2-ylidene) chloro(tricyclohexylphosphine)-(2-oxobenzylidene) ruthenium(II), 1,3-Bis(2,4,6-trimethylphenylimidazolidin-2-ylidene)chloro(tricyclohexylphosphine)-(2-oxo-5-nitrobenzylidene)ruthenium(II), 1,3-Bis(2,4,6-trimethylphenylimidazolidin-2-ylidene)iodo (tricyclohexylphosphine)-(2-oxobenzylidene)ruthenium(II), (1,3-dimesitylimidazolidin-2-ylidene)dichloro(2-((2-ethoxy-2-oxoethylidene)amino)benzylidene)ruthenium(II), (1,3-bis(2,6-diisopropylphenyl)imidazolidin-2-ylidene)dichloro(2-((2-ethoxy-2-oxoethylidene)amino)benzylidene) ruthenium(II), (4-((4-ethyl-4-methylpiperazin-1-ium-1-yl) methyl)-1,3-dimesitylimidazolidin-2-ylidene)dichloro(2-isopropoxybenzylidene)ruthenium(II) chloride, (4-((4-ethyl-4-methylpiperazin-1-ium-1-yl)methyl)-1,3-dimesitylimidazolidin-2-ylidene)dichloro(2-isopropoxybenzylidene)ruthenium(II) hexafluorophosphate, (1,3-dimesityl-4-((trimethylammonio)methyl)imidazolidin-2-ylidene)dichloro(2-isopropoxybenzylidene)ruthenium(II) hexafluorophosphate, (1,3-dimesityl-4-((trimethylammonio)methyl)imidazolidin-2-ylidene)dichloro(2-isopropoxy-5-nitrobenzylidene)ruthenium(II), (1,3-dimesityl-4-((trimethylammonio)methyl)imidazolidin-2-ylidene) dichloro(2-isopropoxybenzylidene)ruthenium(II) tetrafluoroborate, (1,3-bis(2,6-diisopropylphenyl)-4-((4-ethyl-4-methylpiperazin-1-ium-1-yl)methyl)imidazolidin-2-ylidene)dichloro(2-isopropoxybenzylidene)ruthenium(II) chloride, (1,3-bis(2,6-diisopropylphenyl)-4-((4-ethyl-4-methylpiperazin-1-ium-1-yl)methyl)imidazolidin-2-ylidene)dichloro(2-isopropoxybenzylidene)ruthenium(II) hexafluorophosphate, bis(2-(2,6-diethylphenyl)-3,3-dimethyl-2-azaspiro[4.5]decan-1-ylidene)dichloro(3-phenyl-1H-inden-1-ylidene)ruthenium(II) dichloromethane complex, [1,3-Bis(2,6-di-i-propylphenyl)imidazolidin-2-ylidene) (tricyclohexylphosphine)-(2-oxobenzylidene) ruthenium(II) chloride, Bis(tricyclohexylphosphine) [(phenylthio)methylene]ruthenium(II) dichloride, [1,3-Bis (2,4,6-trimethylphenyl)-2-imidazolidinylidene]-[2-[[(2-methylphenyl)imino]methyl]phenolyl]-[3-phenyl-1H-inden-1-ylidene]ruthenium(II) chloride, 1,3-Bis(2,4,6-trimethylphenyl)-2-imidazolidinylidene)(3-phenyl-1H-inden-1-ylidene)(4,5-dichloro-1,3-diethyl-1,3-dihydro-2H-imidazol-2-ylidene)ruthenium(II) dichloride, 3-Phenyl-1H-inden-1-ylidene[bis(i-butylphobane)]ruthenium(II) dichloride, {[2-(i-Propoxy)-5-(N,N-dimethylaminosulfonyl)phenyl]methylene}(tricyclohexylphosphine) ruthenium (II) dichloride, Tricyclohexylphosphine[1,3-bis(2,4,6-trimethylphenyl)-4,5-dihydroimidazol-2-ylidene][(phenylthio) methylene]ruthenium(II) dichloride, Tricyclohexylphosphine[1,3-bis(2,4,6-trimethylphenyl)imidazol-2-ylidene][2-thienylmethylene]ruthenium(II) dichloride, Tricyclohexylphosphine[2,4-dihydro-2,4,5-triphenyl-3H-1,2,4-triazol-3-ylidene][2-thienylmethylene]ruthenium (II) dichloride, Tricyclohexylphosphine[4,5-dimethyl 1,3-bis(2,4,6-trimethylphenyl)imidazol-2-ylidene][2-thienylmethylene]ruthenium(II) dichloride, Tri(i-propoxy) phosphine(3-phenyl-1H-inden-1-ylidene)[1,3-bis(2,4,6-trimethylphenyl)-4,5-dihydroimidazol-2-ylidene]ruthenium (II) dichloride, Dichloro[1,3-bis(2,6-diisopropylphenyl)imidazolidin-2-ylidene][(5-(2-ethoxy-2-oxoethanamido))-(2-isopropoxy)benzylidene]ruthenium(II), Dichloro[1,3-bis(2,6-diisopropylphenyl)-2-imidazolidinylidene][(2-isopropoxy)(5-pentafluorobenzoylamino)benzylidene] ruthenium(II), Dichloro[1,3-bis(2,4,6-trimethylphenyl)-2-imidazolidinylidene]{[5-(2-ethoxy-2-oxoethanamido)]-2-isopropoxybenzylidene}ruthenium(II), Dichloro[1,3-bis(2,4,6-trimethylphenyl)-2-imidazolidinylidene][(2-isopropoxy)(5-pentafluorobenzoylamino)benzylidene] ruthenium(II), (1,3-Bis(2,6-diisopropylphenyl) imidazolidin-2-ylidene)dichloro(2-((1-(methoxy(methyl) amino)-3-methyl-1-oxobutan-2-yl)oxy)benzylidene) ruthenium(II), Dichloro[1,3-bis(2,4,6-trimethylphenyl)-2-imidazolidinylidene](3-phenyl-1H-inden-1-ylidene) (pyridyl)ruthenium(II), Dichloro[1,3-bis(2,4,6-trimethylphenyl)-2-imidazolidinylidene]{[2-(1-methylacetoxy)phenyl]methylene}ruthenium(II), Dichloro [1,3-bis(2,4,6-trimethylphenyl)-2-imidazolidinylidene][(2-isopropoxy)(5-trifluoroacetamido)benzylidene]ruthenium (II), Dichloro[1,3-bis(2,6-diisopropylphenyl)imidazolidin-2-ylidene][(5-isobutoxycarbonylamino)-(2-isopropoxy) benzylidene]ruthenium(II) or Dichloro[1,3-bis(2,6-diisopropylphenyl) imidazolidinylidene](3-phenyl-1H-inden-1-ylidene)(triphenylphosphine)ruthenium(II). Even more particularly, the metathesis catalyst may be selected from the group consisting of (1,3-bis(2,6-diisopropylphenyl) imidazolidin-2-ylidene)dichloro(2-((1-(methoxy(methyl) amino)-1-oxopropan-2-yl)oxy)benzylidene)ruthenium(II), (1,3-bis(2,6-diisopropylphenyl)imidazolidin-2-ylidene) diiodo(2-((1-(methoxy(methyl)amino)-1-oxopropan-2-yl) oxy)benzylidene)ruthenium(II), (1,3-dimesitylimidazolidin-2-ylidene)dichloro(2-isopropoxy-5-nitrobenzylidene) ruthenium(II), Dichloro[1,3-bis(2,4,6-trimethylphenyl)-2-imidazolidinylidene](2-isopropoxyphenylmethylene) ruthenium(II), Benzylidene-bis(tricyclohexylphosphine) dichlororuthenium, Dichloro[1,3-bis(2,6-isopropylphenyl)-2-imidazolidinylidene](2-isopropoxyphenylmethylene) ruthenium(II), [1,3-Bis(2,6-di-i-propylphenyl)imidazolidin-2-ylidene)(2-i-propoxy-5-nitrobenzylidene) ruthenium(II) diiodide, 1,3-Bis(2,6-di-i-propylphenyl)imidazolidin-2-ylidene)(2-i-propoxy-5-nitrobenzylidene) ruthenium(II) dichloride, (1,3-Dimesitylimidazolidin-2-ylidene)diiodo(2-isopropoxy-5-nitrobenzylidene)ruthenium(II), Bis(1-(2,6-diethylphenyl)-3,5,5-trimethyl-3-phenylpyrrolidin-2-ylidene)(3-phenyl-1H-inden-1-ylidene)ruthenium(II) dichloride, (1-(2,6-diethylphenyl)-3,5,5-trimethyl-3-phenylpyrrolidin-2-ylidene)dichloro(2-isopropoxy-5-nitrobenzylidene)ruthenium(II), (1-(2,6-diethylphenyl)-3,5,5-trimethyl-3-phenylpyrrolidin-2-ylidene)diiodo(2-isopropoxy-5-nitrobenzylidene)ruthenium(II), Dichloro[1,3-bis(2-methylphenyl)-2-imidazolidinylidene](2-isopropoxyphenylmethylene)ruthenium(II), 1,3-Bis(2,4,6-trimethylphenyl)-4,5-dihydroimidazol-2-ylidene[2-(i-propoxy)-5-(N,N-dimethylaminosulfonyl)phenyl] methyleneruthenium(II) dichloride (resin supported), Dichloro[1,3-bis(2,4,6-trimethylphenyl)-2-imidazolidinylidene](3-phenyl-1H-inden-1-ylidene)(tricyclohexylphosphine)ruthenium(II), [1,3-Bis(2,4,6-trimethylphenyl)-2-imidazolidinylidene]-[2[[(4-methylphenyl)imino] methyl]-4-nitrophenolyl]-[3-phenyl-1H-inden-1-ylidene] ruthenium(II) chloride, Dichloro[1,3-bis(2,4,6-trimethylphenyl)-2-imidazolidinylidene][[5-[(dimethylamino)sulfonyl]-2-(1-methylethoxy-O)phenyl] methylene-C]ruthenium(II), Dichloro[1-(2,6-diisopropylphenyl)-2,2,4-trimethyl-4-phenyl-5-pyrrolidinylidene](2-isopropoxyphenylmethylene) ruthenium(II), [1,3-Bis(2,6-diisopropylphenyl)-2-imidazolidinylidene]dichloro[(2-isopropoxy)(5-trifluoroacetamido)benzylidene]ruthenium(II), Dichloro[1,3-bis(2,6-diisopropylphenyl)-2-imidazolidinylidene] (benzylidene)(tricyclohexylphosphine)ruthenium(II), Dichloro[1-(2,4,6-trimethylphenyl)-2,2,4-trimethyl-4-phenyl-5-pyrrolidinylidene](2-isopropoxyphenylmethylene)ruthenium(II), Dichloro[1-(2,6-diisopropylphenyl)-2,2,4-trimethyl-4-phenyl-5-pyrrolidinylidene](2-isopropoxyphenylmethylene)ruthenium(II), Dichloro[1,3-bis(2,6-diisopropylphenyl)-2-imidazolidinylidene][(2-isopropoxy)(5-pentafluorobenzoylamino)benzylidene] ruthenium(II), Dichloro[1,3-bis(2,4,6-trimethylphenyl)-2-imidazolidinylidene]{[5-(2-ethoxy-2-oxoethanamido)]-2-isopropoxybenzylidene}ruthenium(II), Dichloro[1,3-bis(2,4,6-trimethylphenyl)-2-imidazolidinylidene][(2-isopropoxy)(5-pentafluorobenzoylamino)benzylidene] ruthenium(II), (1,3-Bis(2,6-diisopropylphenyl) imidazolidin-2-ylidene)dichloro(2-((1-(methoxy(methyl) amino)-3-methyl-1-oxobutan-2-yl)oxy)benzylidene) ruthenium(II), Dichloro[1,3-bis(2,4,6-trimethylphenyl)-2-imidazolidinylidene](3-phenyl-1H-inden-1-ylidene) (pyridyl)ruthenium(II), Dichloro[1,3-bis(2,4,6-trimethylphenyl)-2-imidazolidinylidene][(2-isopropoxy)(5-trifluoroacetamido)benzylidene]ruthenium(II), Dichloro[1,3-bis(2,6-diisopropylphenyl)imidazolidin-2-ylidene][(5-isobutoxycarbonylamino)-(2-isopropoxy)benzylidene] ruthenium(II) and Dichloro[1,3-bis(2,6-diisopropylphenyl)-2-imidazolidinylidene](3-phenyl-1H-inden-1-ylidene) (triphenylphosphine)ruthenium(II).

The metathesis catalyst can be added into the reaction medium of the invention's process in a large range of concentrations. As non-limiting examples, one can cite as metal concentration values those ranging from 2 ppm to 200000 ppm, relative to the total amount of compound of formula (II). Preferably, the metal concentration will be comprised between 10 ppm to 1000 ppm, or even between 30 ppm and 100 ppm. It goes without saying that the process works also with more catalyst. However the optimum concentration of metal will depend, as the person skilled in the art knows, on the nature of the latter, on the nature of the substrates, on the temperature and on the desired time of reaction.

According to any embodiments of the invention, a scavenger may be added to the invention process. In particular, the scavenger may be added after 30 minutes, 1 hour, 2 hours, 3 hours, 10 hours, 20 hours, 24 hours, 36 hours. Non-limiting example of suitable scavengers include amines, 1,4-Bis(2-isocyanopropyl)piperazine, pyridines, imidazoles nitriles (polynitriles), sulfoxides such as DMSO, amides, thiols, $Pb(OAc)_4$, 2-mercaptonicotinic acid (MNA), cysteine, chelating phosphines, triphenylphosphine oxide (TPPO), di(ethylene glycol) vinylether, phosphanetriyltrimethanol (THMP), $Na_2S_2O_5$, $H_2O_2$ or silica-bases heterogenous particles.

The scavenger can be added into the reaction medium of the invention's process in a large range of concentrations. As non-limiting examples, one can cite as scavenger concentration values those ranging from 5 equivalents to 10 equivalents relative to the amount of the metathesis catalyst. It goes without saying that the optimum concentration of scavenger will depend, as the person skilled in the art knows, on the nature of the latter, on the nature of the substrate, of the temperature and on the catalyst used during the process, as well as the desired time of reaction.

The compound of formula (III) can be added into the reaction medium of the invention's process in a large range of concentrations. As non-limiting examples, one can cite as compound of formula (III) concentration values those ranging from 0.5 equivalents to 50 equivalents, or even between 1 equivalent to 5 equivalents, relative to the amount of compound of formula (II). It goes without saying that the optimum concentration of compound of formula (III) will depend, as the person skilled in the art knows, on the nature of the latter, on the nature of compound of formula (II), of the temperature and on the catalyst used during the process, as well as the desired time of reaction.

The invention's process is carried out under batch, semi-batch or continuous conditions.

The reaction can be carried out in the absence of a solvent. When a solvent is required or used for practical reasons, then any solvent current in metathesis reactions can be used for the purposes of the invention. Non-limiting examples include $C_{6-10}$ aromatic solvents such as toluene or xylene; $C_{5-12}$ hydrocarbon solvents such as hexane, heptane, or cyclohexane; $C_{4-8}$ ethers such as tetrahydrofuran, 2-MeTHF or MTBE; $C_{4-10}$ esters such as ethyl acetate and i-PrOAc; $C_{1-2}$ chlorinated hydrocarbon, such as dichloromethane, dichloroethane, or chlorobenzene; $C_{2-6}$ primary or secondary alcohols, such as isopropanol, methanol or ethanol; $C_{2-6}$ polar solvents such as acetone or HOAc and water (neutral/acidic); or mixtures thereof. In particular said solvent can be a solvent such as dichloromethane, toluene or no solvent. The choice of the solvent is a function of the nature of the metathesis catalyst and the compound of formula (II) and (III). The person skilled in the art is well able to select the solvent most convenient in each case to optimize the invention's process.

The temperature of the invention's process may be comprised between −10° C. and 150° C., more preferably in the range comprised between 20° C. and 70° C. Of course, a person skilled in the art is also able to select the preferred temperature as a function of the melting and boiling point of the starting and final products as well as the desired time of reaction or conversion.

The invention's process may be performed under atmospheric pressure or reduced pressure. The invention's process may be performed under inert atmosphere such as nitrogen and/or argon.

The invention's process may lead to the formation of side products such as dimer of compound of formula (II) such as 2,2'-(but-2-ene-1,4-diyl)bis(cyclopentan-1-one) or dimer of compound of formula (III) such as 2,5-dichlorohex-3-ene and hex-3-ene-2,5-diyl diacetate. Most of the side products formed may be recycled in the invention's process. In addition, unreacted starting materials may be also recycled in the invention's process.

According to any embodiment of the invention, the compound of formula (I) may be further converted to compound of formula (IV)

(IV)

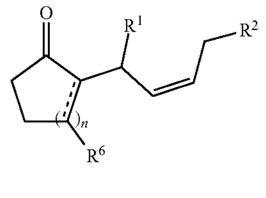

wherein $R^1$, $R^2$ and n have the same meaning as defined above, the dotted line represents a carbon-carbon single bond or carbon-carbon double bond and $R^6$ represents a hydrogen atom, a $C_{1-3}$ alkyl group optionally substituted by a $COOR^6$ group wherein $R^a$ is a $C_{1-3}$ alkyl group. Said compound of formula (IV) may be obtained via the formation of a spirocyclopropyl ring after addition of a base followed by thermal rearrangement (when $R^6$ represents a hydrogen atom and the dotted line represents a double bond). Depending of the nature of $R^6$ further steps may be needed such 1,4 addition and optionally decarboxylation. The person skilled in the art is well aware of the conditions to apply in order to obtain compound of formula (IV) starting from compound of formula (I). Particularly, the formation of a spirocyclopropyl ring may be performed starting with compound of formula (I) with X being a leaving group and, in particular, a halogen atom or a OR' group wherein R' represents a hydrogen atom or a $SO_2R''''$ wherein R'''' represents a methyl, a trifluoromethyl, a phenyl or a tolyl group. In particular, X may be a a halogen atom or a $OSO_2R''''$ wherein R'''' represents a methyl, a trifluoromethyl, a phenyl or a tolyl group. In particular, X may be a chloride atom. For compound of formula (I) with X representing a OR' group wherein R' represents a $C_{1-6}$ alkyl group, a $C_{2-6}$ alkenyl group, a benzyl group, a tetrahydrofuran-2-yl group, a tetrahydro-2H-pyran-2-yl group a trimethylsilyl group, a $CO(O)_mR'$ group, a $CH_2(OR''')$ group or a $CH(OR''')CH_3$ group wherein m is 0 or 1, R'' represents a hydrogen atom, a $C_{1-6}$ alkyl group or a phenyl group and R''' represents a $C_{1-6}$ alkyl group; the invention's process further comprises a step of converting the X group into a leaving group such as a chloride atom or a $OSO_2R''''$ group. Non-limiting and typical manners to perform said conversion are reported herein below in the examples. A side product of formula (I')

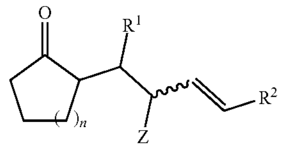

in the form of any one of its stereoisomers or a mixture thereof, and wherein n is an integer between 1 and 4; $R^1$ and $R^2$, independently from each other, represent a hydrogen atom or a $C_{1-3}$ alkyl group and Z is bromide or chloride atom;

may be obtained in combination of compound of formula (I) wherein X is a chloride or bromide atom. Compound of formula (I') may be converted into compound of formula (IV) in the same way than compound of formula (I).

In other words, the process for the preparation of a compound of formula (IV) as defined above comprises the step of i) preparing the compound of formula (I) wherein n is an integer between 1 and 4; $R^1$ and $R^2$, independently from each other, represent a hydrogen atom or a $C_{1-3}$ alkyl group; X represents a halogen atom or a $SO_2R''''$ group wherein R''' represents a methyl, a trifluoromethyl, a phenyl or a tolyl group, comprising the cross metathesis step between compound of the formula (II) as defined above with compound of formula (III) as defined above in the presence of a metathesis catalyst;

ii) preparing a spirocyclopropyl followed by thermolysis;

iii) optionally, 1,4 addition and optionally decarboxylation.

According to any embodiments of the invention, the step i) of preparation of a compound of formula (IV) may further comprise a step of converting the X group into a chloride atom or a $OSO_2R''''$ group, when the cross metathesis is performed with compound of formula (III) wherein X is a OR' group wherein R' represents a $C_{1-6}$ alkyl group, a $C_{2-6}$ alkenyl group, a benzyl group, a tetrahydrofuran-2-yl group, a tetrahydro-2H-pyran-2-yl group a trimethylsilyl group, a $CO(O)_mR''$ group, a $CH_2(OR''')$ group or a $CH(OR''')CH_3$ group wherein m is 0 or 1, R" represents a hydrogen atom, a $C_{1-6}$ alkyl group or a phenyl group and R' represents a $C_{1-6}$ alkyl group.

According to any embodiments of the invention, the preparation of the spirocyclopropyl in step ii) is carried out in a presence of a base.

According to any embodiments of the invention, $R^a$ may represent a methyl or an ethyl group.

For the sake of clarity, by the expression "wherein one dotted line represents a carbon-carbon single bond or carbon-carbon double bond", or the similar, it is meant the normal meaning understood by a person skilled in the art, i.e. that the whole bonding (solid and dotted line) between the carbon atoms connected by said dotted line is a carbon-carbon single or carbon-carbon double bond.

The compound of formula (I) is, generally, novel compounds and present a number of advantages as explained above and shown in the Examples.

Therefore, another object of the present invention is a compound of formula (I)

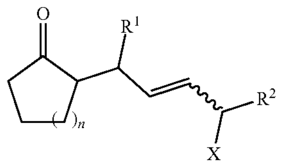

in the form of any one of its stereoisomers or a mixture thereof, and wherein n is an integer between 1 and 4; $R^1$ and $R^2$, independently from each other, represent a hydrogen atom or a $C_{1-3}$ alkyl group; and X represents a halogen atom or a OR' group wherein R' represents a hydrogen atom, a $C_{1-6}$ alkyl group, a $C_{2-6}$alkenyl group, a benzyl group, a trimethylsilyl group, a tetrahydrofuran-2-yl group, a tetrahydro-2H-pyran-2-yl group, a $CO(O)_mR''$ group, a $CH_2(OR''')$ group, a $CH(OR''')CH_3$ group or a $SO_2R''''$ group wherein m is 0 or 1, R" represents a hydrogen atom, a $C_{1-6}$ alkyl group or a phenyl group, R''' represents a $C_{1-6}$ alkyl group and R'''' represents a methyl, a trifluoromethyl, a phenyl or a tolyl group.

According to any embodiment of the invention, the compound of formula (I) is of formula (I) as defined above provide that 2-(4-chlorobut-2-enyl)cyclohexanone, cis-2-(4-hydroxy-2-penten-1-yl)cyclohexanone and cis-2-(4-hydroxy-2-penten-1-yl)cyclopentanone are excluded.

According to any embodiment of the invention, the compound of formula (I) is of formula (I")

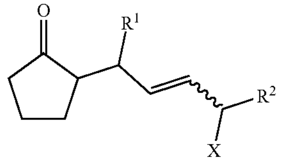

in the form of any one of its stereoisomers or a mixture thereof, and wherein $R^1$, $R^2$ and X have the same meaning as defined above.

Typical manners to execute the invention's process are reported herein below in the examples.

EXAMPLES

The invention will now be described in further detail by way of the following examples, wherein the abbreviations have the usual meaning in the art, the temperatures are indicated in degrees centigrade (° C.). NMR spectra were acquired using either a Bruker Avance II Ultrashield 400 plus operating at 400 MHz, ($^1H$) and 100 MHz ($^{13}C$) or a Bruker Avance III 500 operating at 500 MHz ($^1H$) and 125 MHz ($^{13}C$) or a Bruker Avance III 600 cryoprobe operating at 600 MHz ($^1H$) and 150 MHz ($^{13}C$). Spectra were internally referenced relative to tetramethyl silane 0.0 ppm. $^1H$ NMR signal shifts are expressed in δ ppm, coupling constants (J) are expressed in Hz with the following multiplicities: s, singlet; d, doublet; t, triplet; q, quartet; m, multiplet; b, broad (indicating unresolved couplings) and were interpreted using Bruker Topspin software. $^{13}C$ NMR data are expressed in chemical shift δ ppm and hybridization from DEPT 90 and DEPT 135 experiments, C, quaternary (s); CH, methine (d); $CH_2$, methylene (t); $CH_3$, methyl (q).

Example 1

Cross Metathesis Between 2-allylcyclopentan-1-one and 3-chlorobut-1-ene to Prepare 2-(4-chloropent-2-en-1-yl)cyclopentan-1-one In a 10 mL flask 1 g, (8.05 mmol) 2-allylcyclopentan-1-one was mixed with 2.19 g (24.16 mmol, 3 eq) 3-chlorobut-1-ene at room temperature under Argon atmosphere. 9.2 mg (0.0121 mmol, 0.15 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) was added over 3 hours (3 times 3.05 mg). A gas evolution was observed after each addition of the catalyst. Then, the mixture was stirred over night at room temperature. After the addition of 26 mg (1.5 mol %) SnatchCat® (1,4-Bis(2-isocyanopropyl)piperazine, CAS 51641-96-4) and an hour stirring at room temperature the mixture was filtered through a silica gel column and the solvent was evaporated under reduced pressure. The crude (2.40 g) was purified by a Kugelrohr distillation (45-140° C., 1.6 Torr). 1.43 g (80.0% purity) of 2-(4-chloropent-2-en-1-yl)cyclopentan-1-one (6.13 mmol, 76.1% yield) were obtained as a colorless liquid (containing GC 17.4% 2,5-dichlorohex-3-ene).

$^{13}C$-NMR 2 major isomers ((2E)-2-(4-chloropent-2-en-1-yl)cyclopentan-1-one): 20.63 (one signal, 2 Carbons), 25.34, 25.36, 28.96 29.06 31.87, 32.00, 38.09, 38.12, 48.60, 48.64, 57.95 (one signal, 2 Carbons), 129.27, 129.42, 134.15, 134.18, 220.2 (one signal, 2 Carbons).

$^1$H-NMR (600 MHz, $CDCl_3$) of ((2E)-2-(4-chloropent-2-en-1-yl)cyclopentan-1-one) (2 major isomers): 1.58 (3H, dd, J=6.6 Hz, J=1.5 Hz), 1.74-1.83 (1H, m), 1.97-2.22 (6H, m), 2.28-2.35 (1H, m), 2.45-2.51 (1H, m), 4.49-4.60 (1H, m), 5.63-5.67 (2H, m).

13C-NMR (characteristic signals) of 2 minor isomers (2-(4-chloropent-2-en yl)cyclopentan-1-one): 25.80, 25.84, 26.95, 27.44, 28.82, 29.29, 37.96, 133.39, 133.66, 128.45, 129.07, 219.92, 220.05.

Example 2

Cross Metathesis Between 2-allylcyclopentan-1-one and 3-chlorobut-1-ene to Prepare 2-(4-chloropent-2-en-1-yl)cyclopentan-1-one In a 10 mL flask, 1 g (8.05 mmol) 2-allylcyclopentan-1-one was mixed with 1.46 g (16.11 mmol, 2 eq) 3-chlorobut-1-ene at room temperature under Argon atmosphere. 9.2 mg (0.0121 mmol, 0.15 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) was added over 3 hours (3 times 3.05 mg). A gas evolution was observed after each addition of the catalyst. Then, the mixture was stirred over night at room temperature. After the addition of 26 mg (1.5 mol %) SnatchCat® (1,4-Bis(2-isocyanopropyl)piperazine, CAS 51641-96-4) and an hour stirring at room temperature the mixture was filtered through a silica gel column and the solvent was evaporated under reduced pressure. The crude (2.03 g) was purified by a Kugelrohr distillation (45-140° C., 1.6 Torr. 1.2 g (78.9% purity) of 2-(4-chloropent-2-en-1-yl)cyclopentan-1-one (5.07 mmol, 62.9% yield) were obtained as a colorless liquid (containing GC 15.8% 2,5-dichlorohex-3-ene).

Example 3

Cross Metathesis Between 2-allylcyclopentan-1-one and 3-chlorobut-1-ene to Prepare 2-(4-chloropent-2-en-1-yl)cyclopentan-1-one in Presence of a Solvent In a 100 mL flask 1 g (8.05 mmol) 2-allylcyclopentan-1-one is mixed with 1.46 g (16.11 mmol, 2 eq) 3-chlorobut-1-ene and 40 mL dichloromethane at room temperature under Argon atmosphere. 63 mg (0.0805 mmol, 1 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) is added. Then the mixture was stirred at 40° C. for 4 hours. After the addition of 88.7 mg (5 mol %) SnatchCat® (1,4-Bis(2-isocyanopropyl)piperazine, CAS 51641-96-4) and an hour stirring at room temperature the mixture solvent was evaporated under reduced pressure (2.05 g crude). The crude (2.05 g) was purified by a Kugelrohr distillation (45-140° C., 1.6 Torr). 1.48 g (68.9% purity) of 2-(4-chloropent-2-en-1-yl)cyclopentan-1-one (5.46 mmol, 67.9% yield) were obtained as a colourless liquid (containing GC 11.1% 2,5-dichlorohex-3-ene, 9.6% 2,2'-(but-2-ene-1,4-diyl)bis(cyclopentan-1-one, 1.0% 2-allylcyclopentan one).

Example 4

Cross Metathesis Between 2-allylcyclopentan-1-one and 3-chlorobut-1-ene to Prepare 2-(4-chloropent-2-en-1-yl)cyclopentan-1-one In a 10 mL Schlenk tube 2 g (16.10 mmol) 2-allylcyclopentan-1-one was mixed with 2.92 g (32.21 mmol, 2 eq) 3-chlorobut-1-ene at room temperature under Argon atmosphere. 13 mg (0.0167 mmol, 0.1 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) was added and a gas evolution was observed after addition of the catalyst. The mixture was stirred one hour at room temperature followed by a further addition of 12 mg (0.0154 mmol, 0.1 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6). Again, a gas evolution was observed and the mixture was stirred 3 hours at room temperature. After the addition of 35 mg (1 mol %) SnatchCat® (1,4-Bis(2-isocyanopropyl)piperazine, CAS 51641-96-4) and an hour stirring at room temperature, the crude (4.10 g) was purified by a Kugelrohr distillation. The first fraction (80° C., 1 atm) gives 1.0 g (11.04 mmol) 3-chlorobut-1-ene. The second fraction (45° C.-140° C., 1.5 Torr) gives 1.70 g (54.0% 2-(4-chloropent-2-en-1-yl)cyclopentan-1-one, 1.4% 2,2'-(but-2-ene-1,4-diyl)bis(cyclopentan-1-one), 17.1% 2,5-dichlorohex-3-ene, 5.5% 3-chlorobut-1-ene, 14.0% 2-allylcyclopentan-1-one). The third fraction (45° C.-140° C., 1.5 Torr) gives 0.70 g (GC 86.8% 2-(4-chloropent-2-en-1-yl)cyclopentan-1-one, 3.0% 2,2'-(but-2-ene-1,4-diyl)bis(cyclopentan-1-one)). The last fraction gives 0.43 g 2,2'-(but-2-ene-1,4-diyl)bis(cyclopentan-1-one).

Overall 2-(4-chloropent-2-en-1-yl)cyclopentan-1-one: 1.53 g (8.20 mmol, 51% yield).

Overall 2,2'-(but-2-ene-1,4-diyl)bis(cyclopentan-1-one)): 475 mg (2.16 mmol, 26.8% yield—could be reused in the cross-metathesis reaction)

Overall 2-allylcyclopentan-1-one: 238 mg (1.91 mmol, 11.9% yield—could be reused in the cross-metathesis reaction)

Overall 3-chlorobut-1-ene: 1.09 g (12.04 mmol, 37.4% yield—could be reused in the cross-metathesis reaction)

Overall 2,5-dichlorohex-3-ene: 291 mg (1.90 mmol, 11.8% yield—could be reused in the cross-metathesis reaction)

The spectral data of 2-allylcyclopentan-1-one ($^1$H-NMR) were identical with those published (*Journal of the American Chemical Society* 2011, 133, 2418-2420).

$^{13}$C NMR of 2-allylcyclopentan-1-one (100 MHz, $CDCl_3$): 20.7, 29.0, 33.9, 38.2, 48.6, 116.4, 136.0, 220.5.

$^1$H-NMR (600 MHz, $CDCl_3$) of 2,2'-(but-2-ene-1,4-diyl)bis(cyclopentan-1-one) (2 major isomers): 1.52-1.60 (2H, m), 1.73-1.82 (2H, m), 1.96-2.19 (10H, m), 2.27-2.34 (2H, m), 2.40-2.46 (2H, m), 5.40-5.43 (2H, m).

$^{13}$C NMR of the major isomer 2,2'-(but-2-ene-1,4-diyl)bis(cyclopentan-1-one) (80%) (150 MHz, $CDCl_3$): 20.67 (2C), 28.92 (2C), 32.58, 32.61, 38.27 (2C), 48.94 (2C), 129.40, 129.41, 220.72 (2C).

$^{13}$C NMR of the minor isomers (characteristic signals): 21.05 (2C), 38.16 (2C), 49.07, 49.09, 128.46, 128.43, 220.63 (2C).

$^1$H-NMR (600 MHz, $CDCl_3$) of 2,5-dichlorohex-3-ene: 1.60 (6H, d, J=6.7 Hz), 4.50-4.57 (2H, m), 5.80-5.84 (2H, m).

$^{13}$C NMR of the 2 major isomers 2,5-dichlorohex-3-ene (150 MHz, $CDCl_3$):

(55%) 24.99, 56.51, 133.06.

(45%) 24.82, 56.30, 132.90.

Example 5

Cross Metathesis Between 2-allylcyclopentan-1-one and 3-chlorobut-1-ene to Prepare 2-(4-chloropent-2-en-1-yl)cyclopentan-1-one (from 0.05 mol % to 0.1 mol % of Metathesis Catalyst)

In a 5 mL Schlenk tube 1 g (98.5% purity, 7.93 mmol) freshly distilled 2-allylcyclopentan-1-one was mixed with 1.46 g (15.95 mmol, 2 eq) of freshly distilled 3-chlorobut-1-ene at room temperature under Argon atmosphere and 3.15 mg (0.0040 mmol, 0.05 mol %) GreenCat® (1,3-bis(2,6-diisopropylphenyl)imidazolidin ylidene)dichloro(2-((1-(methoxy(methyl)amino)-1-oxopropan yl)oxy)benzylidene) ruthenium(II); origin: Apeiron; CAS 1448663-06-6) was added (gas evolution was observed). Then the mixture was stirred at room temperature for 1 hour (GC analysis: 51.7% 2-(4-chloropent-2-en-1-yl)cyclopentan-1-one, 16.9% 2,2'-(but-2-ene-1,4-diyl)bis(cyclopentan-1-one, 4.9% 2,5-dichlorohex-3-ene, 23.8% 2-allylcyclopentan-1-one). The mixture was stirred 23 hours at room temperature (GC analysis: 52.5% 2-(4-chloropent-2-en-1-yl)cyclopentan-1-one, 16.3% 2,2'-(but-2-ene-1,4-diyl)bis(cyclopentan-1-one, 4.7% 2,5-dichlorohex-3-ene, 23.9% 2-allylcyclopentan-1-one) followed by a further addition of 3.15 mg (0.0040 mmol, 0.05 mol) GreenCat® (1,3-bis(2,6-diisopropylphenyl)imidazolidin-2-ylidene)dichloro(2-((1-(methoxy (methyl)amino)-1-oxopropan-2-yl)oxy)benzylidene)ruthenium(II); origin: Apeiron; CAS 1448663-06-6). Again, a gas evolution was observed and the mixture was stirred 94 hours at room temperature (GC analysis: 66.9% 2-(4-chloropent-2-en-1-yl)cyclopentan-1-one, 11.0% 2,2'-(but-2-ene-1,4-diyl)bis(cyclopentan-1-one, 11.2% 2,5-dichlorohex-3-ene, 8.2% 2-allylcyclopentan-1-one). After the addition of 8.7 mg SnatchCat® (1,4-Bis(2-isocyanopropyl)piperazine, CAS 51641-96-4) and an hour stirring at room temperature the mixture was filtered through a pad of $SiO_2$ (without addition of solvent).

Example 6

Cross Metathesis Between 2-allylcyclopentan-1-one and 3-chlorobut-1-ene to Prepare 2-(4-chloropent-2-en-1-yl)cyclopentan-1-one (from 0.016 mol % to 0.1 mol % of Metathesis Catalyst)

In a 10 mL Schlenk tube 3 g (98.5% purity, 23.796 mmol) freshly distilled 2-allylcyclopentan-1-one was mixed with 4.41 g (48.167 mmol, 2 eq) of freshly distilled 3-chlorobut-1-ene at room temperature under Argon atmosphere and 3.15 mg (0.0040 mmol, 0.016 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) was added (gas evolution was observed). Then the mixture was stirred at room temperature for 1 hour (GC analysis: 14.4% 2-(4-chloropent-2-en-1-yl)cyclopentan-1-one, 7.5% 2,2'-(but-2-ene-1,4-diyl)bis(cyclopentan-1-one, 0.7% 2,5-dichlorohex-3-ene, 75.7% 2-allylcyclopentan one). The mixture was stirred 23 hours at room temperature (GC analysis: 14.6% 2-(4-chloropent-2-en-1-yl)cyclopentan-1-one, 7.9% 2,2'-(but-2-ene-1,4-diyl)bis(cyclopentan-1-one). 0.7% 2,5-dichlorohex-3-ene, 74.9% 2-allylcyclopentan-1-one) followed by a further addition of 15.75 mg (0.020 mmol, 0.084 mol %) GreenCat® (1,3-bis(2,6-diisopropylphenyl)imidazolidin-2-ylidene)dichloro(2-((1-(methoxy (methyl)amino)-1-oxopropan-2-yl)oxy)benzylidene)ruthenium(II); origin: Apeiron; CAS 1448663-06-6). Again, a gas evolution was observed and the mixture was stirred 94 hours at room temperature (GC analysis: 63.7% 2-(4-chloropent-2-en-1-yl)cyclopentan-1-one, 12.3% 2,2'-(but-2-ene-1,4-diyl)bis(cyclopentan-1-one, 8.7% 2,5-dichlorohex-3-ene, 12.3% 2-allylcyclopentan-1-one). After the addition of 26.5 mg SnatchCat® (1,4-Bis(2-isocyanopropyl)piperazine, CAS 51641-96-4) and an hour stirring at room temperature the mixture was filtered through a pad of $SiO_2$ (without addition of solvent).

Example 7

Cross Metathesis Between 2-allylcyclopentan-1-one and 3-chlorobut-1-ene to Prepare 2-(4-chloropent-2-en-1-yl)cyclopentan-1-one (from 0.033 mol % to 0.1 mol % of Metathesis Catalyst)

In a 10 mL Schlenk tube 2 g (98.7% purity, 15.896 mmol) freshly distilled 2-allylcyclopentan-1-one was mixed with 2.92 g (31.893 mmol, 2 eq) of freshly distilled 3-chlorobut-1-ene at room temperature under Argon atmosphere and 4.2 mg 0.00535 mmol, 0.033 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) was added (gas evolution was observed). Then the mixture was stirred at room temperature for 1 hour (GC analysis: 27.6% 2-(4-chloropent-2-en-1-yl)cyclopentan-1-one, 12.6% 2,2'-(but-2-ene-1,4-diyl)bis(cyclopentan-1-one, 1.3% 2,5-dichlorohex-3-ene, 56.3% 2-allylcyclopentan-1-one). The mixture was stirred 69 hours at room temperature (GC analysis: 27.6% 2-(4-chloropent-2-en-1-yl)cyclopentan-1-one, 12.8% 2,2'-(but-2-ene-1,4-diyl)bis(cyclopentan-1-one, 1.3% 2,5-dichlorohex-3-ene, 56.3% 2-allylcyclopentan-1-one) followed by a further addition of 8.4 mg (0.0107 mmol, 0.067 mol %) GreenCat® (1,3-bis(2,6-diisopropylphenyl)imidazolidin-2-ylidene)dichloro(2-((1-(methoxy (methyl)amino)-1-oxopropan-2-yl)oxy)benzylidene)ruthenium(II); origin: Apeiron; CAS 1448663-06-6). Again, a gas evolution was observed and the mixture was stirred 24 hours at room temperature (GC analysis: 67.0% 2-(4-chloropent-2-en yl)cyclopentan-1-one, 9.5% 2,2'-(but-2-ene-1,4-diyl) bis(cyclopentan-1-one, 11.8% 2,5-dichlorohex-3-ene, 8.8% 2-allylcyclopentan-1-one). After the addition of 17.7 mg SnatchCat® (1,4-Bis(2-isocyanopropyl)piperazine, CAS 51641-96-4) and an hour stirring at room temperature the mixture was filtered through a pad of $SiO_2$ (without addition of solvent).

The crude (11.416 g, 64.9% 2-(4-chloropent-2-en-1-yl) cyclopentan-1-one) of the 3 reactions (examples 5-7) with overall 6 g 2-allylcyclopentan-1-one (48.32 mmol) and 8.79 g 3-chlorobut-1-ene (97.07 mmol) (using 37.8 mg GreenCat®, (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6), 49.2 mg SnatchCat® (1,4-Bis(2-isocyanopropyl)piperazine, CAS 51641-96-4)) was purified by a Kugelrohr distillation (85° C., atm, 30 min to 130° C., 1.1 Torr, 17 min). 5.304 g 2-(4-chloropent-2-en-1-yl)cyclopentan-1-one (27.39 mmol, 58.8% yield) were obtained as a colorless liquid.

Overall 2-(4-chloropent-2-en-1-yl)cyclopentan-1-one: 5.304 g (27.39 mmol, 58.8% yield) as a colorless liquid.

Overall 2,2'-(but-2-ene-1,4-diyl)bis(cyclopentan-1-one)): 780 mg (3.53 mmol, 14.6% yield— could be reused in the cross-metathesis reaction)

Overall 2-allylcyclopentan-1-one: 810 mg (6.52 mmol, 13.5% yield—could be reused in the cross-metathesis reaction)

Overall 3-chlorobut-1-ene: 2.711 g (29.94 mmol, 30.8% yield—could be reused in the cross-metathesis reaction). 2.32 g of 3-chlorobut-1-ene were lost because of its volatility.

Overall 2,5-dichlorohex-3-ene: 814 mg (6.53 mmol, 13.5% yield—could be reused in the cross-metathesis reaction)

Example 8

Cross Metathesis Between 2-allylcyclopentan-1-one and 3-chlorobut-1-ene to Prepare 2-(4-chloropent-2-en-1-yl)cyclopentan-1-one In a 5 mL Schlenk tube 1 g (92.3% purity, 7.473 mmol) 2-allylcyclopentan-1-one was mixed with 1.46 g (16.124 mmol, 2 eq) 3-chlorobut-1-ene at room temperature under Argon atmosphere. 11.66 mg (0.0121 mmol, 0.15 mol %) (1,3-bis(2,6-diisopropylphenyl)imidazolidin-2-ylidene) diiodo(2-((1-(methoxy(methyl)amino)-1-oxopropan-2-yl) oxy)benzylidene)ruthenium(II) (CAS 2380295-90-7) was added over 3 hours (3 times 3.87 mg). A gas evolution was observed after each addition of the catalyst. Then, the mixture was stirred over night at room temperature and was analyzed by GC (GC analysis: addition of SnatchCat® (1,4-Bis(2-isocyanopropyl)piperazine, CAS 51641-96-4) to the sample, stirring at room temperature and filtration through a pad of $SiO_2$).

GC analysis after 24 hours at room temperature: 6.3% 2-allylcyclopentan-1-one, 63.4% 2-(4-chloropent-2-en-1-yl) cyclopentan-1-one, 12.8% 2,2'-(but-2-ene-1,4-diyl)bis(cyclopentan-1-one, 8.7% 2,5-dichlorohex-3-ene.

Example 9

Cross Metathesis Between 2-allylcyclopentan-1-one and 3-chlorobut-1-ene to Prepare 2-(4-chloropent-2-en-1-yl)cyclopentan-1-one In a 5 mL Schlenk tube 1 g (92.3% purity, 7.473 mmol) 2-allylcyclopentan-1-one was mixed with 1.46 g (16.124 mmol, 2 eq) 3-chlorobut-1-ene at room temperature under Argon atmosphere. 8.59 mg (0.0121 mmol, 0.15 mol %) Dichloro[1,3-bis(2,6-isopropylphenyl)-2-imidazolidinylidene](2-isopropoxyphenylmethylene)ruthenium(II) (CAS 635679-24-2) was added over 3 hours (3 times 2.86 mg). A gas evolution was observed after each addition of the catalyst. Then, the mixture was stirred over night at room temperature and was analyzed by GC (GC analysis: addition of SnatchCat® (1,4-Bis(2-isocyanopropyl)piperazine, CAS 51641-96-4) to the sample, stirring at room temperature and filtration through a pad of $SiO_2$).

GC analysis after 24 hours at room temperature: 11.5% 2-allylcyclopentan-1-one, 55.9% 2-(4-chloropent-2-en-1-yl) cyclopentan-1-one, 16.9% 2,2'-(but-2-ene-1,4-diyl)bis(cyclopentan-1-one, 6.2% 2,5-dichlorohex-3-ene.

Example 10

Cross Metathesis Between 2-allylcyclopentan-1-one and 3-chlorobut-1-ene to Prepare 2-(4-chloropent-2-en-1-yl)cyclopentan-1-one In a 5 mL Schlenk tube 1 g (92.6% purity, 7.457 mmol) 2-allylcyclopentan-1-one was mixed with 1.46 g (16.011 mmol, 2.1 eq) 3-chlorobut-1-ene at room temperature under Argon atmosphere. 11.33 mg (0.0121 mmol, 0.15 mol %) [1,3-Bis(2,6-di-i-propylphenyl)imidazolidin-2-ylidene)(2-i-propoxy-5-nitrobenzylidene) ruthenium(II) diiodide (CAS 1874265-00-5) was added over 3 hours (3 times 3.78 mg). A gas evolution was observed after each addition of the catalyst. Then, the mixture was stirred over night at room temperature and was analyzed by GC (GC analysis: addition of SnatchCat® (1,4-Bis(2-isocyanopropyl)piperazine, CAS 51641-96-4) to the sample, stirring at room temperature and filtration through a pad of $SiO_2$).

GC analysis after 24 hours at room temperature: 5.6% 2-allylcyclopentan-1-one, 64.7% 2-(4-chloropent-2-en-1-yl) cyclopentan-1-one, 11.6% 2,2'-(but-2-ene-1,4-diyl)bis(cyclopentan-1-one, 10.7% 2,5-dichlorohex-3-ene.

Example 11

Cross Metathesis Between 2-allylcyclopentan-1-one and 3-chlorobut-1-ene to Prepare 2-(4-chloropent-2-en-1-yl)cyclopentan-1-one General Procedure:

In a 10 mL Schlenk tube with reflux condenser 250 mg (98.2% purity, 1.977 mmol) 2-allylcyclopentan-1-one was mixed with 358 mg (3.954 mmol, 2 eq) of 3-chlorobut-1-ene in 2.5 mL dichloromethane at room temperature under Argon atmosphere and 1 mol % catalyst was added. Then the mixture was stirred at room temperature for 1 hour and analyzed by GC (GC analysis: addition of SnatchCat® (1,4-Bis(2-isocyanopropyl)piperazine, CAS 51641-96-4) to the sample, stirring at room temperature and filtration through a pad of $SiO_2$). The mixture was warmed up to 40° C. (reflux) and was analyzed by GC after 1 hour (GC analysis: addition of SnatchCat® (1,4-Bis(2-isocyanopropyl)piperazine, CAS 51641-96-4) to the sample, stirring at room temperature and filtration through a pad of $SiO_2$). After the addition of 4 mol % catalyst the mixture stirred further 2 hours at 40° C. (reflux) and analyzed by GC (GC analysis: addition of SnatchCat® (1,4-Bis(2-isocyanopropyl)piperazine, CAS 51641-96-4) to the sample, stirring at room temperature and filtration through a pad of $SiO_2$).

Cross Metathesis with (2-(2,6-Diethylphenyl)-3,3-dimethyl-2-azaspiro[4.5]decan-1-yl)(2-isopropoxy-5-nitrobenzylidene)ruthenium(II) dichloride GC analysis after 1 hour at room temperature and 3 hours at 40° C. (5 mol %): 8.3% 2-allylcyclopentan-1-one, 45.5% 2-(4-chloropent-2-en-1-yl)cyclopentan-1-one, 25.2% 2,2'-(but-2-ene-1,4-diyl)bis(cyclopentan-1-one, 5.6% 2,5-dichlorohex-3-ene.

Cross Metathesis with (1,3-dimesitylimidazolidin-2-ylidene)dichloro(2-isopropoxy-5-nitrobenzylidene) ruthenium(II) (CAS 502964-52-5)

GC analysis after 1 hour at room temperature and 3 hours at 40° C. (5 mol %): 0.9% 2-allylcyclopentan-1-one, 53.4% 2-(4-chloropent-2-en-1-yl)cyclopentan-1-one, 5.6% 2,2'-(but-2-ene-1,4-diyl)bis(cyclopentan-1-one, 21.1% 2,5-dichlorohex-3-ene.

Cross Metathesis with (1,3-Dimesitylimidazolidin-2-ylidene)diiodo(2-isopropoxy-5-nitrobenzylidene) ruthenium(II) (CAS 1874264-99-9)

GC analysis after 1 hour at room temperature and 1 hour at 40° C. (1 mol %): 10.3% 2-allylcyclopentan-1-one, 55.3%

2-(4-chloropent-2-en-1-yl)cyclopentan-1-one, 15.6% 2,2'-(but-2-ene-1,4-diyl)bis(cyclopentan-1-one, 8.4% 2,5-dichlorohex-3-ene.

Cross Metathesis with Dichloro[1,3-bis(2,4,6-trimethylphenyl)-2-imidazolidinylidene](2-isopropoxyphenylmethylene)ruthenium(II) (CAS 301224-40-8)

GC analysis after 1 hour at room temperature and 1 hour at 40° C.: 3.0% 2-allylcyclopentan-1-one, 63.3% 2-(4-chloropent-2-en-1-yl)cyclopentan-1-one, 10.1% 2,2'-g (but-2-ene-1,4-diyl)bis(cyclopentan-1-one, 17.0% 2,5-dichlorohex-3-ene.

Cross Metathesis with Benzylidene-bis(tricyclohexylphosphine)dichlororuthenium (CAS 172222-30-9)

GC analysis after 1 hour at room temperature and 1 hour at 40° C. (1 mol %): 2.6% 2-allylcyclopentan-1-one, 64.0% 2-(4-chloropent-2-en-1-yl)cyclopentan-1-one, 9.8% 2,2'-(but-2-ene-1,4-diyl)bis(cyclopentan-1-one, 17.2% 2,5-dichlorohex-3-ene.

GC analysis after 1 hour at room temperature and 3 hours at 40° C. (5 mol %): 1.5% 2-allylcyclopentan-1-one, 65.0% 2-(4-chloropent-2-en-1-yl)cyclopentan-1-one, 9.8% 2,2'-(but-2-ene-1,4-diyl)bis(cyclopentan-1-one, 16.3% 2,5-dichlorohex-3-ene.

Cross Metathesis with Bis(1-(2,6-diethylphenyl)-3,5,5-trimethyl-3-phenylpyrrolidin-2-ylidene)(3-phenyl-1H-inden-1-ylidene)ruthenium(II) dichloride (CAS 2055540-61-7)

GC analysis after 1 hour at room temperature and 3 hours at 40° C. (5 mol %): 4.6% 2-allylcyclopentan-1-one, 60.6% 2-(4-chloropent-2-en-1-yl)cyclopentan-1-one, 6.7% 2,2'-(but-2-ene-1,4-diyl)bis(cyclopentan-1-one, 6.1% 2,5-dichlorohex-3-ene.

Cross Metathesis with (1-(2,6-Diethylphenyl)-3,5,5-trimethyl-3-phenylpyrrolidin-2-ylidene)(2-isopropoxy-5-nitrobenzylidene)ruthenium(II) dichloride (CAS 2106819-64-9)

GC analysis after 1 hour at room temperature and 3 hours at 40° C. (5 mol %): 0.4% 2-allylcyclopentan-1-one, 64.3% 2-(4-chloropent-2-en-1-yl)cyclopentan-1-one, 6.8% 2,2'-(but-2-ene-1,4-diyl)bis(cyclopentan-1-one, 10.4% 2,5-dichlorohex-3-ene.

Cross Metathesis with (1-(2,6-Diethylphenyl)-3,5,5-trimethyl-3-phenylpyrrolidin-2-ylidene)(2-isopropoxy-5-nitrobenzylidene)ruthenium(II) diiodide GC analysis after 1 hour at room temperature and 3 hours at 40° C. (5 mol %): 1.2% 2-allylcyclopentan-1-one, 44.3% 2-(4-chloropent-2-en-1-yl)cyclopentan-1-one, 29.4% 2,2'-(but-2-ene-1,4-diyl)bis(cyclopentan-1-one, 9.8% 2,5-dichlorohex-3-ene.

Cross Metathesis with Dichloro[1,3-bis(2,4,6-trimethylphenyl)-2-imidazolidinylidene](benzylidene)(tricyclohexylphosphine)ruthenium(II) (CAS 246047-72-3)

GC analysis after 1 hour at room temperature and 3 hours at 40° C. (5 mol %): 0.9% 2-allylcyclopentan-1-one, 61.6%

2-(4-chloropent-2-en-1-yl)cyclopentan-1-one, 7.1% 2,2'-(but-2-ene-1,4-diyl)bis(cyclopentan-1-one, 17.1% 2,5-dichlorohex-3-ene.

Cross Metathesis with Dichloro[1,3-bis(2-methylphenyl)-2-imidazolidinylidene](2-isopropoxyphenylmethylene)ruthenium(II) (CAS 927429-61-6)

GC analysis after 1 hour at room temperature and 3 hours at 40° C. (5 mol %): 2.5% 2-allylcyclopentan-1-one, 66.0% 2-(4-chloropent-2-en-1-yl)cyclopentan-1-one, 5.6% 2,2'-(but-2-ene-1,4-diyl)bis(cyclopentan-1-one, 13.8% 2,5-dichlorohex-3-ene.

Cross Metathesis with 1,3-bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (Resin Supported)

GC analysis after 1 hour at room temperature and 3 hours at 35° C. (5 mol %): 3.9% 2-allylcyclopentan-1-one, 60.1% 2-(4-chloropent-2-en-1-yl)cyclopentan-1-one, 13.7% 2,2'-(but-2-ene-1,4-diyl)bis(cyclopentan-1-one, 14.5% 2,5-dichlorohex-3-ene.

Cross Metathesis with Dichloro[1,3-bis(2,4,6-trimethylphenyl)-2-imidazolidinylidene][[5-[(dimethylamino)sulfonyl]-2-(1-methylethoxy-O)phenyl]methylene-C]ruthenium(II) (CAS 918870-76-5)

GC analysis after 1 hour at room temperature and 3 hours at 35° C. (5 mol %): 2.5% 2-allylcyclopentan-1-one, 56.1% 2-(4-chloropent-2-en-1-yl)cyclopentan-1-one, 8.5% 2,2'-(but-2-ene-1,4-diyl)bis(cyclopentan-1-one, 19.9% 2,5-dichlorohex-3-ene.

Cross Metathesis with Dichloro[1,3-Bis(2-methylphenyl)-2-imidazolidinylidene](benzylidene)(tricyclohexylphosphine)ruthenium(II) (CAS 927429-60-5)

GC analysis after 1 hour at room temperature and 3 hours at 35° C. (5 mol %): 15.2% 2-allylcyclopentan-1-one, 49.9% 2-(4-chloropent-2-en-1-yl)cyclopentan-1-one, 16.7% 2,2'-(but-2-ene-1,4-diyl)bis(cyclopentan-1-one, 6.2% 2,5-dichlorohex-3-ene.

Cross Metathesis with Dichloro[1,3-bis(2,4,6-trimethylphenyl)-2-imidazolidinylidene](3-phenyl-1H-inden-1-ylidene)(tricyclohexylphosphine)ruthenium(II) (CAS 536724-67-1)

GC analysis after 1 hour at room temperature and 3 hours at 40° C. (5 mol %): 1.6% 2-allylcyclopentan-1-one, 59.8% 2-(4-chloropent-2-en-1-yl)cyclopentan-1-one, 8.9% 2,2'-(but-2-ene-1,4-diyl)bis(cyclopentan-1-one, 14.8% 2,5-dichlorohex-3-ene.

Cross Metathesis with Dichloro[1,3-bis(2,4,6-trimethylphenyl)-2-imidazolidinylidene](3-methyl-2-butenylidene)(dipyridine)ruthenium(II) (CAS 357186-58-4)

GC analysis after 1 hour at room temperature and 3 hours at 35° C. (5 mol %): 15.1% 2-allylcyclopentan-1-one, 47.9%

2-(4-chloropent-2-en-1-yl)cyclopentan-1-one, 17.8% 2,2'-(but-2-ene-1,4-diyl)bis(cyclopentan-1-one, 7.4% 2,5-dichlorohex-3-ene.

Cross Metathesis with [1,3-Bis(2,4,6-trimethylphenyl)-4-[(trimethylammonio)methyl]imidazolidin-2-ylidene]-(2-i-propoxy-5-nitrobenzylidene)dichlororuthenium(II) chloride (CAS 1452227-72-3)

GC analysis after 1 hour at room temperature and 3 hours at 35° C. (5 mol %): 4.6% 2-allylcyclopentan-1-one, 58.2% 2-(4-chloropent-2-en-1-yl)cyclopentan-1-one, 15.8% 2,2'-(but-2-ene-1,4-diyl)bis(cyclopentan-1-one, 10.1% 2,5-dichlorohex-3-ene.

Cross Metathesis with [1,3-Bis(2,6-diisopropylphenyl)-2-imidazolidinylidene]dichloro[(2-isopropoxy)(5-trifluoroacetamido)benzylidene]ruthenium(II) (CAS 1212008-99-5)

GC analysis after 1 hour at room temperature (1 mol %): 12.1% 2-allylcyclopentan-1-one, 59.6% 2-(4-chloropent-2-en-1-yl)cyclopentan-1-one, 10.5% 2,2'-(but-2-ene-1,4-diyl)bis(cyclopentan-1-one, 7.6% 2,5-dichlorohex-3-ene.

GC analysis after 1 hour at room temperature and 1 hour at 35° C. (1 mol %): 2.7% 2-allylcyclopentan-1-one, 71.1% 2-(4-chloropent-2-en-1-yl)cyclopentan-1-one, 6.7% 2,2'-(but-2-ene-1,4-diyl)bis(cyclopentan-1-one, 15.0% 2,5-dichlorohex-3-ene.

Example 12

Cross Metathesis Between 2-allylcyclopentan-1-one and but-3-en-2-yl acetate to Prepare 5-(2-oxocyclopentyl)pent-3-en-2-yl acetate In a 20 mL Schlenk tube, 5 g (98.2% purity, 39.54 mmol) 2-allylcyclopentan-1-one was mixed with 9.938 g (98.1% purity, 85.414 mmol, 2 eq) but-3-en-2-yl acetate at room temperature under Argon atmosphere. 46.6 mg (0.0593 mmol, 0.15 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) was added over 3 hours (15.5 mg each hour) and the mixture was stirred for 24 hours at room temperature. 65.4 mg (0.296 mmol) SnatchCat® (1,4-Bis(2-isocyanopropyl)piperazine, CAS 51641-96-4) were added to the mixture and stirring was continued 1 hour at room temperature (GC analysis: 4.3% allylcyclopentan-1-one, 22.5% but-3-en-2-yl acetate, 42.6% 5-(2-oxocyclopentyl)pent-3-en-2-yl acetate, 4.8% 2,2'-(but-2-ene-1,4-diyl)bis(cyclopentan-1-one, 15.9% hex-3-ene-2,5-diyl diacetate). The mixture was filtered through a pad of $SiO_2$ (12.254 g crude) and was purified by a Kugelrohr distillation (40 C.°-170° C., 0.39 Torr, 15 min).

Overall 5-(2-oxocyclopentyl)pent-3-en-2-yl acetate: 5.71 g (27.15 mmol, 68.7% yield)

Overall 2,2'-(but-2-ene-1,4-diyl)bis(cyclopentan-1-one): 0.690 g (3.13 mmol, 15.8% yield—could be reused in the cross-metathesis reaction)

Overall 2-allylcyclopentan-1-one: 511 mg (4.10 mmol, 10.4% yield—could be reused in the cross-metathesis reaction)

Overall hex-3-ene-2,5-diyl diacetate: 2.00 g (9.989 mmol, 23.4% yield—could be reused in the cross-metathesis reaction)

Overall but-3-en-2-yl acetate: 2.303 g (20.17 mmol, 23.6% yield—could be reused in the cross-metathesis reaction)

$^1$H-NMR (600 MHz, $CDCl_3$) of 5-(2-oxocyclopentyl)pent-3-en-2-yl acetate (2 major isomers): 1.25-1.31 (3H, m), 1.49-1.59 (1H, m), 1.73-1.84 (1H, m), 1.96-2.21 (5H, m), 2.04 (3H, s), 2.27-2.35 (1H, m), 2.46-2.52 (1H, m), 5.26-5.33 (1H, m), 5.48-5.53 (1H, m), 5.61-5.68 (1H, m).

$^{13}$C NMR of 5-(2-oxocyclopentyl)pent-3-en-2-yl acetate (2 major isomers, 100 MHz, $CDCl_3$): 20.31, 20.39, 20.64 (2C), 21.43 (2C), 29.95, 29.00, 32.18, 32.26, 38.15 (2C), 48.65. 48.69, 70.83. 70.85, 129.97, 130.10, 131.57. 131.62, 170.35 (2C), 220.40, 220.42.

$^{13}$C NMR (characteristic signal): 48.84, 48.94, 66.79, 66.92, 129.60, 129.81, 130.97, 131.05.

$^1$H-NMR (600 MHz, $CDCl_3$) of the 2 isomers of hex-3-ene-2,5-diyl diacetate 1.31 (6H, d, J=4.6 Hz), 2.06 (6H, s), 5.32-5.39 (2H, m), 5.68-5.70 (2H, m).

$^{13}$C NMR of the 2 isomers of hex-3-ene-2,5-diyl diacetate (100 MHz, $CDCl_3$): 20.09 (2C), 21.36 (2C), 69.96, 70.00, 131.04, 131.14, 170.26 (2C).

Example 13

Cross Metathesis Between 2-allylcyclopentan-1-one and but-3-en-2-ol to Prepare 2-(4-hydroxypent-2-en-1-yl)cyclopentan-1-one In a 30 mL Schlenk tube, 10 g (98.2% purity, 79.087 mmol) 2-allylcyclopentan-1-one was mixed with 11.405 g (98.1% purity, 158.17 mmol, 2 eq) but-3-en-2-ol at room temperature under Argon atmosphere. 91.1 mg (0.1186 mmol, 0.15 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) was added over 3 hours (31.04 mg each hour) and the mixture was stirred for 24 hours at room temperature. 130.7 mg (0.593 mmol) SnatchCat® (1,4-Bis(2-isocyanopropyl)piperazine, CAS 51641-96-4) were added to the mixture and stirring was continued 1 hour at room temperature (GC analysis 38% allylcyclopentan-1-one and hex-3-ene-2,5-diol ratio 68/32, 22.9% 3-buten-2-ol, 27.9% 2-(4-hydroxypent-2-en-1-yl)cyclopentan-1-one, 4.4% 2,2'-(but-2-ene-1,4-diyl)bis(cyclopentan-1-one). The mixture was filtered through a pad of $SiO_2$ (16.28 g crude, (GC analysis: 48.9% allylcyclopentan-1-one and hex-3-ene-2,5-diol ratio 68/32, 6.5% 3-buten-2-ol, 36.3% 2-(4-hydroxypent-2-en-1-yl)cyclopentan-1-one, 2.8% 2,2'-(but-2-ene-1,4-diyl)bis(cyclopentan-1-one) and was purified by a Kugelrohr distillation (40° C.-170° C., 0.39 Torr, 15 min).

Overall 2-(4-hydroxypent-2-en-1-yl)cyclopentan-1-one: 5.656 g (33.62 mmol, 42.5% yield)

Overall 2,2'-(but-2-ene-1,4-diyl)bis(cyclopentan-1-one): 0.494 g (2.24 mmol, 5.6% yield— could be reused in the cross-metathesis reaction)

Overall 2-allylcyclopentan-1-one and hex-3-ene-2,5-diol ratio 68/32: 7.45 g (5.06 g 2-allylcyclopentan-1-one, 40.7 mmol, 51.4% yield—could be reused in the cross-metathesis reaction, 2.38 g hex-3-ene-2,5-diol, 20.48 mmol, 25.9% yield—could be reused in the cross-metathesis reaction)

Overall but-3-en-2-ol: 0.277 g (3.13 mmol, 3.9% yield—could be reused in the cross-metathesis reaction)

$^1$H-NMR (600 MHz, $CDCl_3$) of 2-(4-hydroxypent-2-en-1-yl)cyclopentan-1-one (2 isomers): 1.24-1.27 (3H, d, J=6.3 Hz), 1.51-1.61 (1H, m), 1.64-1.71 (1H, OH), 1.72-1.84 (1H, m), 1.96-2.23 (5H, m), 2.27-2.35 (1H, m), 2.44-2.50 (1H, m), 4.23-4.30 (1H, m), 5.56-5.61 (2H, m).

$^{13}C$ NMR of the 2 major isomers (>90% E) 2-(4-hydroxy-pent-2-en-1-yl)cyclopentan-1-one (90 MHz, $CDCl_3$): 20.64 (2C), 23.45, 23.47, 29.04 (2C), 32.21 (2C), 38.17 (2C), 48.77, 48.80, 68.56, 68.66, 127.57, 127.64, 136.28, 136.30, 220.58 (2C).

$^{13}C$ NMR (characteristic signals) of 2 minor isomers 2-(4-hydroxypent-2-en-1-yl)cyclopentan-1-one (90 MHz, $CDCl_3$): 48.94, 49.08, 127.10, 127.93, 135.46, 136.00.

$^1H$-NMR (600 MHz, $CDCl_3$) of the 2 isomers of hex-3-ene-2,5-diol: 1.26 (6H, dd, J=6.4 Hz, J=3.8 Hz), 4.27-4.34 (2H, m), 5.71 (2H, dq, J=13.1 Hz, J=1.4 Hz).

$^{13}C$ NMR of the 2 isomers of hex-3-ene-2,5-diol (90 MHz, $CDCl_3$): 523.29 (2C), 23.30 (2C), 68.11 (2C), 68.18 (2C), 133.78 (2C), 133.87 (2C).

Example 14

Cross Metathesis Between 2-allylcyclopentan-1-one and 3-(1-butoxyethoxy)but-1-ene to Prepare 2-(4-(1-butoxyethoxy)pent-2-en-11-yl)cyclopentan-1-one In a 5 mL Schlenk tube, 0.250 g (98.2% purity, 1.977 mmol) 2-allylcyclopentan-1-one was mixed with 0.680 g (3.954 mmol, 2 eq) 3-(1-butoxyethoxy)but-1-ene at room temperature in 2.5 mL dichloromethane under Argon atmosphere. 15.5 mg (0.0198 mmol, 1 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) was added and the mixture was stirred for 24 hours at room temperature. The mixture was analyzed by GC (GC analysis: addition of SnatchCat® (1,4-Bis(2-isocyanopropyl)piperazine, CAS 51641-96-4) to the sample, stirring at room temperature and filtration through a pad of $SiO_2$).

GC analysis: 1.2% 2-allylcyclopentan-1-one, 73.8% 2-(4-(1-butoxyethoxy)pent-2-en-1-yl)cyclopentan-1-one, 8.3% 2,2'-(but-2-ene-1,4-diyl)bis(cyclopentan-1-one, 1.7% 6,8,11,13-tetramethyl-5,7,12,14-tetraoxaoctadec-9-ene.

Characteristic signals of a purified sample (85% purity)

2-(4-(1-butoxyethoxy)pent-2-en-1-yl)cyclopentan-1-one (4 major diastereomers)

Characteristic Signals:

$^{13}C$ NMR (100 MHz, $CDCl_3$): 13.93, 13.95, 19.42, 19.47, 20.36, 20.59, 20.65, 21.43, 22.02, 22.06, 29.05, 29.06, 29.07, 29.09, 31.9, 32.1, 32.26, 32.30, 32.33, 32.35, 38.16, 38.17, 48.74, 48.76, 48.80, 48.84, 63.55, 63.61, 65.04, 65.11, 71.72, 71.84, 72.38, 72.41, 96.94, 96.98, 98.07, 98.08, 127.99, 128.02, 129.5, 129.6, 134.1, 134.9, 220.38, 220.41, 220.50, 220.52.

3-(1-butoxyethoxy)but-1-ene could be prepared from but-3-en-2-ol and 1-(vinyloxy)butane (cat $CF_3COOH$ or PPTS, THF, room temperature 5 hours, R. Menicagli, C. Malanga, M. Dell'Innocenti, L. Lardicci *J. Org. Chem.* 1987, 52, 5700-5704).

Characteristic signals of a purified (85% purity) sample of 3-(1-butoxyethoxy)but-1-ene (diastereomers).

$^{13}C$ NMR (100 MHz, $CDCl_3$): 13.93 (2C), 19.41, 20.34, 20.53, 21.04, 21.76, 31.89, 32.08, 63.80, 65.02, 72.26, 73.08, 114.61, 115.73, 140.22, 140.97

Example 15

Cross Metathesis Between 2-allylcyclopentan-1-one and (but-3-en-2-yloxy)trimethylsilane to Prepare 2-(4-((trimethylsilyl)oxy)pent-2-en-1-yl)cyclopentan-1-one In a 5 mL Schlenk tube, 0.159 g (98.2% purity, 1.257 mmol) 2-allylcyclopentan-1-one was mixed with 0.389 g (2.515 mmol, 2 eq) (but-3-en-2-yloxy)trimethylsilane (CAS 18269-41-5) at room temperature in 1.6 mL dichloromethane under Argon atmosphere. 9.9 mg (0.0126 mmol, 1 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) was added and the mixture was stirred for 24 hours at room temperature. The mixture was analyzed by GC (GC analysis: addition of SnatchCat® (1,4-Bis(2-isocyanopropyl)piperazine, CAS 51641-96-4) to the sample, stirring at room temperature and filtration through a pad of $SiO_2$).

GC analysis: 0.7% 2-allylcyclopentan-1-one, 43.0% 2-(4-((trimethylsilyl)oxy)pent-2-en-1-yl)cyclopentan-1-one, 33.2% 2,2'-(but-2-ene-1,4-diyl)bis(cyclopentan-1-one, 5.1% 2,2,4,7,9,9-hexamethyl-3,8-dioxa-2,9-disiladec-5-ene.

Characteristic signals of a purified sample (96% purity) 2-(4-((trimethylsilyl)oxy)pent-2-en-1-yl)cyclopentan-1-one (2 major diastereomers)

$^1H$-NMR (600 MHz, $CDCl_3$) of 2-(4-((trimethylsilyl)oxy)pent-2-en-1-yl)cyclopentan-1-one (2 isomers): 0.11 (9H, s), 1.20 (3H, d, J=6.4 Hz), 1.51-1.60 (1H, m), 1.73-1.82 (1H, m), 1.96-2.04 (2H, m), 2.06-2.21 (3H, m), 2.27-2.35 (1H, m), 2.44-2.50 (1H, m), 4.22-4.27 (1H, m), 5.49-5.51 (2H, m).

$^{13}C$ NMR of the 2 major isomers 2-(4-((trimethylsilyl)oxy)pent-2-en-1-yl)cyclopentan-1-one (90 MHz, $CDCl_3$): 0.20 (6C), 20.62 (2C), 24.51 (2C), 28.95, 29.02, 32.22, 32.22 38.15, 38.17, 48.81, 48.85, 68.93, 68.97 126.26, 126.28, 136.56, 136.60, 220.60, 220.62.

$^{13}C$ NMR (characteristic signals) of the 2 minor isomers 2-(4-((trimethylsilyl)oxy)pent-2-en-1-yl)cyclopentan-1-one (90 MHz, $CDCl_3$): 125.25, 125.29, 136.50, 136.70.

Example 16

Cross Metathesis Between (E)-2-(pent-2-en-1-yl)cyclopentanone and 3-chlorobut-1-ene to Prepare 2-(4-chloropent-2-en-1-yl)cyclopentan-1-one In a 10 mL Schlenk tube, 2 g (13.14 mmol) (E)-2-(pent-2-en-1-yl)cyclopentanone was mixed with 2.38 g (26.28 mmol, 2 eq) 3-chlorobut-1-ene at room temperature under Argon atmosphere. 51 mg (0.0657 mmol, 0.5 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) was added and the mixture was stirred for 2 hours at room temperature. After the addition of 87 mg (5 mol %) SnatchCat® (1,4-Bis(2-isocyanopropyl)piperazine, CAS 51641-96-4) the mixture was stirred one hour at room temperature. The crude (3.98 g, GC analysis of crude: 29% 2-(4-chloropent-2-en-1-yl)cyclopentan-1-one, 12.6% 2,2'-(but-2-ene-1,4-diyl)bis(cyclopentan-1-one), 8.6% 2,5-dichlorohex-3-ene, 23.9% 2-chlorohex-3-ene, 8.4% (E)-2-(pent-2-en-1-yl)cyclopentanone) was purified by a Kugelrohr distillation. The first fraction (75° C., 1 atm) gave 0.400 g (4.43 mmol) 3-chlorobut-1-ene. The second fraction (45°

C.-140° C., 1.6 Torr) gave 2.72 g (GC 34.2% 2-(4-chloropent-2-en-1-yl)cyclopentan-1-one, 24.3% 2-chlorohex-3-ene, 10.8% 2,5-dichlorohex-3-ene, 11.8% (E)-2-(pent-2-en-1-yl)cyclopentanone, 11.2% 2-allylcyclopentan-1-one. The third fraction gave 0.63 g (10.3% 2-(4-chloropent-2-en-1-yl)cyclopentan-1-one, 79.0% 2,2'-(but-2-ene-1,4-diyl)bis(cyclopentan-1-one))

Overall 2-(4-chloropent-2-en-1-yl)cyclopentan-1-one: 994 mg (5.32 mmol, 40.5% yield)

Overall 2,2'-(but-2-ene-1,4-diyl)bis(cyclopentan-1-one) 498 mg (2.26 mmol, 34.4% yield— could be reused in the cross-metathesis reaction)

Overall 3-chlorobut-1-ene: 0.400 g (4.43 mmol, 16.8% yield— could be reused in the cross-metathesis reaction)

Overall 2-allylcyclopentan-1-one: 0.305 g (2.45 mmol, 18.7% yield—could be reused in the cross-metathesis reaction)

Overall 2,5-dichlorohex-3-ene: 0.294 g (1.92 mmol, 14.6% yield— could be reused in the cross-metathesis reaction)

Overall 2-chlorohex-3-ene: 0.662 g (5.57 mmol, 21.2% yield— could be reused in the cross-metathesis reaction).

2-Chlorohex-3-ene (for the characterization) could be prepared from (E)-hex-3-ene and 2 eq 3-chlorobut-1-ene by cross metathesis using 1 mol % GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) (without solvent at room temperature).

$^1$H-NMR (600 MHz, $CDCl_3$) of the of the 2 isomers of 2-chlorohex-3-ene: 0.98 (3H, t, J=7.3 Hz) 1.00 (3H, t, J=7.4 Hz), 1.59 (3H, d, J=6.6 Hz), 1.72 (3H, d, J=6.5 Hz), 1.79-1.86 (2H, m), 2.03-2.08 (2H, m), 4.26-4.29 (1H, m), 4.52-4.57 (1H, m), 5.52-5.60 (2H, m), 5.68-5.76 (2H, m).

$^{13}$C NMR (125 MHz, $CDCl_3$) of the of the 2 isomers of 2-chlorohex-3-ene: 11.10, 13.15, 17.51, 24.93, 25.48, 31.99, 58.63, 65.26, 128.41, 131.19, 132.05, 134.07.

Example 17

Cross Metathesis Between 2,2'-(but-2-ene-1,4-diyl)bis(cyclopentan-1-one) and 3-chlorobut-1-ene to Prepare 2-(4-chloropent-2-en-1-yl)cyclopentan-1-one In a 10 mL Schlenk tube, 1 g (4.54 mmol) 2,2'-(but-2-ene-1,4-diyl)bis(cyclopentan-1-one) was mixed with 1.64 g (18.15 mmol, 4 eq) 3-chlorobut-1-ene at room temperature under Argon atmosphere. 18 mg (0.0227 mmol, 0.5 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) was added and the mixture was stirred for 1 hours at room temperature. After the addition of 25 mg (2.5 mol %) SnatchCat® (1,4-Bis(2-isocyanopropyl)piperazine, CAS 51641-96-4) the mixture was stirred 30 min at room temperature. The crude (2.23 g, GC analysis of crude: 30.7% 2-(4-chloropent-2-en-1-yl)cyclopentan-1-one, 46.8% 2,2'-(but-2-ene-1,4-diyl)bis(cyclopentan-1-one, 8.6% 2,5-dichlorohex-3-ene, 10.7% 2-allylcyclopentan-1-one) was purified by a Kugelrohr distillation. The first fraction (80° C., 1 atm) gave 0.500 g (5.52 mmol) 3-chlorobut-1-ene. The second fraction (45° C.-130° C., 1 atm) gave 0.800 g (GC 51.2% 2-(4-chloropent-2-en-1-yl)cyclopentan-1-one, 3.4% 2,2'-(but-2-ene-1,4-diyl)bis(cyclopentan-1-one, 16.7% 2,5-dichlorohex-3-ene, 19.5% 2-allylcyclopentan-1-one. The third fraction gave 0.510 g (7.0% 2-(4-chloropent-2-en-1-yl)cyclopentan-1-one, 81.3% 2,2'-(but-2-ene-1,4-diyl)bis(cyclopentan-1-one, 1.9% 2-allylcyclopentan-1-one)

Overall 2-(4-chloropent-2-en-1-yl)cyclopentan-1-one: 446 mg (2.39 mmol, 52.6% yield)

Overall 2,2'-(but-2-ene-1,4-diyl)bis(cyclopentan-1-one: 442 mg (2.01 mmol, 44.3% yield—could be reused in the cross-metathesis reaction)

Overall 3-chlorobut-1-ene: 0.500 g (5.52 mmol, 30.3% yield—could be reused in the cross-metathesis reaction)

Overall 2-allylcyclopentan-1-one: 0.157 g (1.26 mmol, 13.9% yield—could be reused in the cross-metathesis reaction)

Overall 2,5-dichlorohex-3-ene: 0.294 g (1.92 mmol, 14.6% yield—could be reused in the cross-metathesis reaction)

Example 18

Cross Metathesis Between 2,2'-(but-2-ene-1,4-diyl)bis(cyclopentan-1-one) and 5-dichlorohex-3-ene to Prepare 2-(4-chloropent-2-en-1-yl)cyclopentan-1-one In a 5 mL Schlenk tube, 200 mg (0.908 mmol) 2,2'-(but-2-ene-1,4-diyl)bis(cyclopentan-1-one) was mixed with 166 mg (1.089 mmol, 1.2 eq) 2,5-dichlorohex-3-ene at room temperature under Argon atmosphere. 18 mg (0.027 mmol, 3 mol %) NitroGrela ((1,3-dimesitylimidazolidin-2-ylidene)dichloro(2-isopropoxy nitrobenzylidene)ruthenium(II), Apeiron CAS 502964-52-5) was added. Then, the mixture was stirred 6 hours at room temperature and was analyzed by GC (GC analysis: addition of SnatchCat® (1,4-Bis(2-isocyanopropyl)piperazine, CAS 51641-96-4) to the sample, stirring at room temperature and filtration through a pad of $SiO_2$).

GC analysis after 6 hours at room temperature: 8.4% 2-(4-chloropent-2-en-1-yl)cyclopentan-1-one, 65.2% 2,2'-(but-2-ene-1,4-diyl)bis(cyclopentan-1-one, 26.4% 2,5-dichlorohex-3-ene.

2,2'-(but-2-ene-1,4-diyl)bis(cyclopentan-1-one) (97% purity) could be prepared from 2-allylcyclopentan-1-one by cross metathesis using 0.3 mol % GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) (without solvent, 2 hours at room temperature).

2,5-dichlorohex-3-ene (98% purity) could be prepared from 3-chlorobut-1-ene by cross metathesis using 0.2 mol % GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II); origin: Apeiron; CAS 1448663-06-6) (without solvent, 2 hours at room temperature).

Example 19

Cross Metathesis Between 2-(3-methylbut-2-en-1-yl)cyclopentan-1-one and 3-chlorobut-1-ene to Prepare 2-(4-chloropent-2-en-1-yl)cyclopentan-1-one In a 10 mL Schlenk tube, 2 g (13.14 mmol) 2-(3-methylbut-2-en-1-yl)cyclopentan-1-one was mixed with 2.38 g (26.28 mmol, 2 eq) 3-chlorobut-1-ene at room temperature under Argon atmosphere. 52 mg (0.0657 mmol, 0.5 mol %) GreenCat® (1,3-bis(2,6-diisopropylphenyl)imidazolidin-2-ylidene)dichloro(2-((1-(methoxy(methyl)amino)-1-oxopropan-2-yl)oxy)benzylidene)ruthenium(II);

origin: Apeiron; CAS 1448663-06-6) was added and the mixture was stirred for 2 hours at room temperature. After two hours at room temperature 72 mg (2.5 mol %) SnatchCat® (1,4-Bis(2-isocyanopropyl)piperazine, CAS 51641-96-4) were added to the mixture and stirring was continued 30 min at room temperature. The crude (4.02 g, GC analysis: 12.5% 2-(4-chloropent-2-en yl)cyclopentan-1-one, 3.1 2,2'-(but-2-ene-1,4-diyl)bis(cyclopentan-1-one, 20.3% 2,5-dichlorohex-3-ene, 53.3% 2-(3-methylbut-2-en-1-yl)cyclopentan-1-one, 4.3% 2-allylcyclopentan-1-one, 4.0% 4-chloro-2-methylpent-2-ene) was purified by a Kugelrohr distillation. The first fraction (90° C., 1 atm) gave 0.500 g (5.52 mmol) 3-chlorobut-1-ene. The second fraction (45° C.-130° C., 1 atm) gave 0.750 g (GC 2.0% 2-(4-chloropent-2-en-1-yl)cyclopentan-1-one, 6.0% 2,5-dichlorohex-3-ene, 88.0% 2-(3-methylbut-2-en-1-yl)cyclopentan-1-one, 1.4% 2-allylcyclopentan-1-one. The third fraction gave 1.050 g (56.2% 2,5-dichlorohex-3-ene, 33.0% 2-(3-methylbut-2-en-1-yl)cyclopentan-1-one, 10.7% 2-allylcyclopentan-1-one). The fourth fraction gives 0.700 g (42.6% 2-(4-chloropent-2-en-1-yl)cyclopentan-1-one, 43.0% 2-(3-methylbut-2-en-1-yl)cyclopentan-1-one). The last fraction gave 0.250 g (14.4% 2-(4-chloropent-2-en-1-yl)cyclopentan-1-one, 8% 2-(3-methylbut-2-en-1-yl)cyclopentan-1-one, 48.2% 2,2'-(but-2-ene-1,4-diyl)bis(cyclopentan-1-one).

Overall 2-(4-chloropent-2-en-1-yl)cyclopentan-1-one: 0.349 mg (1.87 mmol, 14.2% yield)

Overall 2,2'-(but-2-ene-1,4-diyl)bis(cyclopentan-1-one): 0.121 g (0.55 mmol, 8.3% yield— could be reused in the cross-metathesis reaction Overall 2-(3-methylbut-2-en-1-yl)cyclopentan-1-one: 1.328 g (8.72 mmol, 66.4% yield—could be reused in the cross-metathesis reaction)

Overall 3-chlorobut-1-ene: 0.500 g (5.52 mmol, 21.0% yield—could be reused in the cross-metathesis reaction)

Overall 2,5-dichlorohex-3-ene: 0.635 g (4.15 mmol, 31.6% yield—could be reused in the cross-metathesis reaction)

Overall 2-allylcyclopentan-1-one: 0.111 mg (0.893 mmol, 6.8% yield—could be reused in the cross-metathesis reaction)

Overall 4-chloro-2-methylpent-2-ene: 0.161 mg (1.35 mmol, 5.2% yield— could be reused in the cross-metathesis reaction)

Example 20

Cross Metathesis Between 2-allylcyclopentan-1-one (insitu formed 2,2'-but-2-ene-1,4-diyl)bis(cyclopentan-1-one) and 5-dichlorohex-3-ene to Prepare 2-(4-chloropent-2-en yl)cyclopentan-1-one In a 5 mL Schlenk tube, 200 mg (1.582 mmol, 98.2% purity) 2-allylcyclopentan-1-one was mixed with 537 mg (90% purity, 3.16 mmol, 2 eq) 2,5-dichlorohex-3-ene at room temperature under Argon atmosphere in 2 mL dichloromethane. 65 mg (0.0791 mmol, 5 mol %) Hoveyda-Grubbs Catalyst® M71 SIPr ([1,3-Bis(2,6-diisopropylphenyl)-2-imidazolidinylidene]dichloro[(2-isopropoxy)(5-trifluoroacetamido)benzylidene]ruthenium(II), CAS Number 1212008-99-5) was added in two portions (1 mol % at room temperature, 1 hour stirring at room temperature and 1 hour at 40° C., 4 mol % at 40° C., 2 hours stirring at 40° C.). Then, the mixture was analyzed by GC (GC analysis: addition of SnatchCat® (1,4-Bis(2-isocyanopropyl)piperazine, CAS 51641-96-4) to the sample, stirring at room temperature and filtration through a pad of $SiO_2$).

GC analysis (without 2,5-dichlorohex-3-ene) after 1 hour at room temperature and 3 hours at 40° C. (5 mol %): 0.9% 2-allylcyclopentan-1-one, 52.0% 2-(4-chloropent-2-en-1-yl)cyclopentan-1-one, 30.3% 2,2'-(but-2-ene-1,4-diyl)bis(cyclopentan-1-one. GC analysis showed that 2,2'-(but-2-ene-1,4-diyl)bis(cyclopentan-1-one) was formed before the formation of 2-(4-chloropent-2-en-1-yl)cyclopentan-1-one.

In a 5 mL Schlenk tube, 200 mg (1.582 mmol, 98.2% purity) 2-allylcyclopentan-1-one was mixed with 537 mg (90% purity, 3.16 mmol, 2 eq) 2,5-dichlorohex-3-ene at room temperature under Argon atmosphere in 2 mL dichloromethane. 45 mg (0.0791 mmol, 5 mol %) Dichloro[1,3-bis(2-methylphenyl)-2-imidazolidinylidene](2-isopropoxyphenylmethylene)ruthenium(II) (Hoveyda-Grubbs Catalyst® M72 SI(o-Tol) (C571), Stewart-Grubbs catalyst, CAS Number 927429-61-6): was added in two portions (1 mol % at room temperature, 1 hour stirring at room temperature and 1 hour at 40° C., 4 mol % at 40° C., 2 hours stirring at 40° C.). Then, the mixture was analyzed by GC (GC analysis: addition of SnatchCat® (1,4-Bis(2-isocyanopropyl)piperazine, CAS 51641-96-4) to the sample, stirring at room temperature and filtration through a pad of $SiO_2$).

GC analysis (without 2,5-dichlorohex-3-ene) after 1 hour at room temperature and 3 hours at 40° C. (5 mol %): 3% 2-allylcyclopentan-1-one, 30.2% 2-(4-chloropent-2-en yl)cyclopentan-1-one, 44.7% 2,2'-(but-2-ene-1,4-diyl)bis(cyclopentan-1-one. GC analysis showed that 2,2'-(but-2-ene-1,4-diyl)bis(cyclopentan-1-one) was formed before the formation of 2-(4-chloropent-2-en-1-yl)cyclopentan-1-one.

Example 21

Transformation of 5-(2-oxocyclopentyl)pent-3-en-2-yl acetate, 2-(4-(1-butoxyethoxy)pent-2-en-1-yl)cyclopentan-1-one or 2-(4-((trimethylsilyl)oxy)pent-2-en-1-yl)cyclopentan-1-one to 2-(4-hydroxypent-2-en-1-yl)cyclopentan-1-one 5-(2-oxocyclopentyl)pent-3-en-2-yl acetate, 2-(4-(1-butoxyethoxy)pent-2-en-1-yl)cyclopentan-1-one or 2-(4-((trimethylsilyl)oxy)pent-2-en-1-yl)cyclopentan-1-one can be fully deprotected to 2-(4-hydroxypent-2-en-1-yl)cyclopentan-1-one by using standard deprotection protocols (NaOH, MeOH for 5-(2-oxocyclopentyl)pent-3-en-2-yl acetate, AcOH, $H_2O$ for 2-(4-(1-butoxyethoxy)pent-2-en-1-yl)cyclopentan-1-one, $CF_3COOH$, MeOH for 2-(4-((trimethylsilyl)oxy)pent-2-en-1-yl)cyclopentan-1-one).

J. E. Baeckvall, S. E. Bystroem, R. E. Nordberg. *J. Org. Chem.* 1984, 49, 4619-4631 (NaOH, MeOH).

N. Pendem, C. Douat, P. Claudon, M. Laguerre, S. Castano, B. Desbat, D. Cavagnat, E. Ennifar, B. Kauffmann, G. Guichard, *J. Am. Chem. Soc.* 2013, 135, 4884-4892 ($CF_3COOH$, MeOH).

B. B. Snider, X. Gao, *Org. Lett.* 2005, 7, 4419-4422 (AcOH, $H_2O$).

Example 22

Preparation of 2-(4-chloropent-2-en-1-yl)cyclopentan-1-one and (E)-2-(2-chloropent-3-en-1-yl)cyclopentan-1-one from 2-(4-hydroxypent-2-en-1-yl)cyclopentan-1-one 200 mg (96.5% purity, 1.148 mmol) of 2-(4-hydroxypent-2-en-1-yl)cyclopentan-1-one were stirred under water cooling in 0.50 mL EtOH. 0.721 g (9.18 mmol, 8 eq) Acetyl chloride was added slowly and the mixture was stirred one hour at room temperature (complete conversion of starting material). 5 mL $Et_2O$ were added and the mixture was washed twice with 2 mL of a saturated aqueous $NaHCO_3$ solution. After a filtration through a plug of $SiO_2$ (for drying) the solvent was evaporated under reduced (40° C., 15 mbar). 204 mg (93% purity, 1.016 mmol) of a 64/36 mixture of 2-(4-chloropent-2-en yl)cyclopentan-1-one and (E)-2-(2-chloropent-3-en-1-yl)cyclopentan-1-one were isolated (88% yield).

Example 23

Preparation of 2-(4-chloropent-2-en-1-yl)cyclopentan-1-one and (E)-2-(2-chloropent-3-en-1-yl)cyclopentan-1-one from 5-(2-oxocyclopentyl)pent-3-en-2-yl acetate 200 mg (97.5% purity, 0.9269 mmol) of 5-(2-oxocyclopentyl)pent-3-en-2-yl acetate were stirred under water cooling in 0.41 mL EtOH. 0.582 g (7.42 mmol, 8 eq) Acetyl chloride was added slowly and the mixture was stirred one hour at room temperature (complete conversion of starting material). 5 mL dichloromethane were added and the solvent was evaporated under reduced pressure (40° C., 150 mbar). This procedure was repeated twice. 178 mg (91% purity, 0.870 mmol) of a 63/37 mixture of 2-(4-chloropent-2-en-1-yl)cyclopentan-1-one and (E)-2-(2-chloropent-3-en-1-yl)cyclopentan-1-one were isolated (94% yield).

$^{13}$C-NMR 2 major isomers ((2E)-2-(4-chloropent-2-en-1-yl)cyclopentan-1-one): 20.63 (one signal, 2 Carbons), 25.34, 25.36, 28.96 29.06 31.87, 32.00, 38.09, 38.12, 48.60, 48.64, 57.95 (one signal, 2 Carbons), 129.27, 129.42, 134.15, 134.18, 220.2 (one signal, 2 Carbons).

$^{13}$C-NMR (characteristic signals) of 2 minor isomers (2-(4-chloropent-2-en-1-yl)cyclopentan-1-one): 25.80, 25.84, 26.95, 27.44, 28.82, 29.29, 37.96, 133.39, 133.66, 128.45, 129.07, 219.92, 220.05.

$^{1}$H-NMR (600 MHz, $CDCl_3$) of the of the 2 isomers of (E)-2-(2-chloropent-3-en-1-yl)cyclopentan-1-one: 1.71 (3H, d, J=6.5 Hz), 1.74-2.39 (9H, m), 4.45-4.59 (1H, m), 5.49-5.58 (1H, m), 5.71-5.78 (1H, m).

$^{13}$C NMR (125 MHz, $CDCl_3$) of the of the 2 isomers of (E)-2-(2-chloropent-3-en-1-yl)cyclopentan-1-one: 17.51, 17.53, 20.69, 20.73, 29.62, 30.06, 37.76, 37.88, 38.75, 39.11, 46.79, 46.94, 61.57, 61.80, 128.91, 129.11, 131.60, 131.87, 220.14, 220.19.

Example 24

Preparation of 1-((E)-prop-1-en-1-yl)spiro[2.4]heptan-4-one 400 mg KOH were mixed with 4 g Ethanol and 600 mg water. 0.485 g of this solution (0.691 mmol KOH) was added slowly under stirring at 0° C. 4.51 g of this solution was added slowly under stirring at room temperature to 864 mg (4.628 mmol) of 2-(4-chloropent-2-en-1-yl)cyclopentan-1-one. The mixture was warmed up to room temperature and was further stirred 1.5 hours. After neutralization with a 5% aqueous HCl solution EtOAc was added. The aqueous phase was separated and the organic phase was washed with a saturated aqueous $NaHCO_3$ solution and a saturated aqueous NaCl solution. The solvent was evaporated under reduced pressure and 1.08 g crude were obtained. A Kugelrohr distillation of the crude gave 528 mg (3.515 mmol, 76% yield) of (1SR,3RS)-1-((E)-prop-1-en-1-yl)spiro[2.4]heptan-4-one/(1RS,3RS)-1-((E)-prop-1-en-1-yl)spiro[2.4]heptan-4-one/(Z)-1-(prop-1-en-1-yl)spiro[2.4]heptan-4-one (ratio 82/9/9).

$^{13}$C-NMR major isomer (1SR,3RS)-1-((E)-prop-1-en-1-yl)spiro[2.4]heptan-4-one $^{13}$C NMR (90 MHz, $CDCl_3$): 18.1, 21.0, 23.0, 27.7, 31.8, 35.9, 38.7, 128.1, 128.4, 218.6.

$^{13}$C-NMR minor isomers (1RS,3RS)-1-((E)-prop-1-en-1-yl)spiro[2.4]heptan-4-one and (Z)-1-(prop-1-en-1-yl)spiro[2.4]heptan-4-one:

$^{13}$C NMR (150 MHz, $CDCl_3$): 17.9, 21.1, 22.4, 33.8, 36.3, 36.5, 39.8, 126.1, 128.1, 217.1.

$^{13}$C NMR (150 MHz, $CDCl_3$): 13.1, 21.2, 22.8, 31.3, 33.9, 36.8, 39.8, 125.0, 127.4, 216.9.

The spectral data ($^{1}$H-NMR) were identical with those published (*Helvetica Chimica Acta,* 1978, 2524).

Example 25

Preparation of 1-((E)-prop-1-en-1-yl)spiro[2.4]heptan-4-one from a mixture of 2-(4-chloropent-2-en-1-yl)cyclopentan-1-one and (E)-2-(2-chloropent-3-en-1-yl)cyclopentan-1-one 1.6 g KOH were mixed with 16 g Ethanol and 2.4 g water. 0.485 g of this solution (0.691 mmol KOH) was added slowly under stirring at 0° C. to 141 mg (91.4% purity, 0.691 mmol) of 63/37 mixture of 2-(4-chloropent-2-en-1-yl)cyclopentan-1-one and (E)-2-(2-chloropent-3-en-1-yl)cyclopentan-1-one. GC analysis ((E)-2-(2-chloropent-3-en yl)cyclopentan-1-one reacted faster) after 1.5 h gave with 96% conversion a mixture of (1SR,3RS)-1-((E)-prop-1-en-1-yl)spiro[2.4]heptan-4-one/(1RS,3RS)-1-((E)-prop-1-en yl)spiro[2.4]heptan-4-one/(Z)-1-(prop-1-en-1-yl)spiro[2.4]heptan-4-one (ratio 83/8/10).

Example 26

Preparation of 1-((E)-prop-1-en-1-yl)spiro[2.4]heptan-4-one 19.2 mg (0.804 mmol, 1.5 eq) NaH were washed with heptane and 3 mL of THF were added. After heating to 65° C. 100 mg (0.536 mmol) of 2-(4-chloropent-2-en-1-yl)cyclopentan-1-one were added slowly under stirring. After 2 hours at 65° C. a full conversion was observed (GC analysis: 89% of (1SR,3RS)-1-((E)-prop-1-en-1-yl)spiro[2.4]heptan-4-one/(1RS,3RS)-1-((E)-prop-1-en-1-yl)spiro[2.4]heptan-4-one/(Z)-1-(prop-1-en-1-yl)spiro[2.4]heptan-4-one (ratio 15/63/19).

Example 27

Preparation of 1-((E)-prop-1-en-1-yl)spiro[2.4]heptan-4-one from (E)-5-(2-oxocyclopentyl)pent-3-en-2-yl methanesulfonate ((E)-5-(2-oxocyclopentyl)pent-3-en-2-yl methanesulfonate (prepared from 2-(4-hydroxypent-2-en-1-yl)cyclopentan-1-one (MsCl, $NEt_3$, dichloromethane) and used as a crude) could be fully transformed (KOH, EtOH, $H_2O$) to a mixture of (1SR,3RS)-1-((E)-prop-1-en-1-yl)spiro[2.4]heptan-4-one and (1RS,3RS)-1-((E)-prop-1-en-1-yl)spiro[2.4]heptan-4-one (minor isomer).

$^{13}$C-NMR characteristic signals of isomers of ((E)-5-(2-oxocyclopentyl)pent-3-en-2-yl methanesulfonate): 80.3, 80.6, 81.3, 81.5.

Example 28

Preparation of (Z)-2-(pent-2-en-1-yl)cyclopent-2-en-1-one

A Glass (Quartz) column (15 cm) filled with 5 g of quartz rings and a heating system (Pyrolysis Oven), was connected to a cooling condenser on the bottom of the column. The glass column was heated up to 400° C. (with the Pyrolysis Oven). A mixture of 1.13 g (7.51 mmol) of (1SR,3RS)-1-((E)-prop-1-en-1-yl)spiro[2.4]heptan-4-one/(1RS,3RS)((E)-prop-1-en-1-yl)spiro[2.4]heptan-4-one/(Z)-1-(prop-1-en-1-yl)spiro[2.4]heptan-4-one (82/9/9) obtained in example 24 and 6 mL toluene was introduced slowly from the top with a syringe pump under an Argon flow from the top. The crude was collected at the bottom with a cooled 25 mL flask. The solvent of the crude was evaporated under reduced pressure and 836 mg (5.56 mmol) 74% yield of (Z)-2-(pent-2-en-1-yl)cyclopent-2-en-1-one and 242 mg (1.61 mmol 21% yield of recycled starting material) of a mixture of 1SR,3RS)-1-((E)-prop-1-en-1-yl)spiro[2.4]heptan-4-one/(1RS,3RS)-1-((E)-prop-1-en-1-yl)spiro[2.4]heptan-4-one/(Z)-1-(prop-1-en-1-yl)spiro[2.4]heptan-4-one (52/8/40) were obtained by GC analysis of the crude.

(Z)-2-(pent-2-en-1-yl)cyclopent-2-en-1-one could be separated by column chromatography (80 g $SiO_2$, eluent Cyclohexane/EtOAc 9/1).

Preparation of Methyljasmonate and (Z)-Jasmone: Both these compounds were obtained from (Z)-2-(pent-2-en-1-yl)cyclopent-2-en-1-one by known methods; for experimental details, see references: G. Blichi, B. Egger, *J. Org. Chemistry* 1971, 36, 2021. P. Jaunky, J. Buirey, C. Mahaim, *Flavour Fragr. J.* 2017, 32, 388-391.

$^{13}C$ NMR of (Z)-2-(pent-2-en-1-yl)cyclopent-2-en-1-one (90 MHz, CDC13): 14.2, 20.5, 22.8, 26.5, 34.6, 124.4, 133.7, 145.3, 157.6, 209.6.

The spectral data were identical with those published ($^1H$-NMR):

G. Büchi, B. Egger, *J. Org. Chemistry* 1971, 36, 2021. H. Kataoka, T. Yamada, K. Goto, J. Tsuji, An efficient synthetic method of methyl (±)-jasmonate. *Tetrahedron.* 1987, 43, 4107-4112.

The invention claimed is:

1. A process for the preparation of a compound of formula (I)

(I)

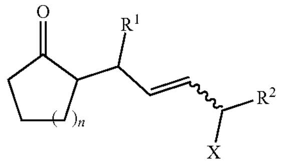

in the form of any one of its stereoisomers or a mixture thereof, and wherein n is an integer between 1 and 4; $R^1$ and $R^2$, independently from each other, represent a hydrogen atom or a $C_{1-3}$ alkyl group; and X represents a halogen atom or a OR' group wherein R' represents a hydrogen atom, a $C_{1-6}$ alkyl group, a $C_{2-6}$ alkenyl group, a benzyl group, a trimethylsilyl group, a tetrahydrofuran-2-yl group, a tetrahydro-2H-pyran-2-yl group, a $CO(O)_mR''$ group, a $CH_2(OR''')$ group, a $CH(OR''')CH_3$ group or a $SO_2R''''$ group wherein m is 0 or 1, R'' represents a hydrogen atom, a $C_{1-6}$ alkyl group or a phenyl group, R''' represents a $C_{1-6}$ alkyl group and R'''' represents a methyl, a trifluoromethyl, a phenyl or a tolyl group;

by cross metathesis between compound of formulae (II)

(II)

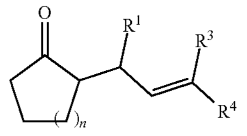

in the form of any one of its stereoisomers or a mixture thereof, and wherein n and $R^1$ have the same meaning as defined in formula (I) and $R^3$ and $R^4$, independently from each other, represent a hydrogen atom or a $C_{1-6}$ alkyl group optionally substituted by an oxo group;

with compound of formula (III)

(III)

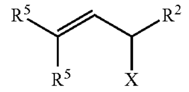

in the form of any one of its stereoisomers or a mixture thereof, and wherein X and $R^2$ have the same meaning as defined in formula (I) and $R^5$, independently from each other, represent a hydrogen atom or a $C_{1-5}$ alkyl group optionally substituted by a X group as defined above;

in the presence of a metathesis catalyst.

2. The process according to claim 1, wherein n is 1.

3. The process according to claim 1, wherein $R^1$ is a hydrogen atom.

4. The process according to claim 1, wherein $R^2$ represents a methyl or an ethyl group.

5. The process according to claim 1, wherein X may be a halogen atom, a OR' group wherein R' represents a hydrogen atom, an acetyl group, a methoxymethyl group, a ethoxymethyl group, 1-butoxyethyl group, a 1-ethoxyethyl group or a trimethylsilyl group.

6. The process according to claim 1, wherein X is a halogen atom.

7. The process according to claim 1, wherein $R^3$, $R^4$ and $R^5$ represent a hydrogen atom.

8. The process according to claim 1, wherein the metathesis catalyst is a Ruthenium-based catalyst.

9. The process according to claim 1, wherein the metathesis catalyst is selected from the group consisting of 1,3-bis(2,6-diisopropylphenyl)imidazolidin-2-ylidene)dichloro(2-((1-(methoxy(methyl)amino)-1-oxopropan-2-yl)oxy)benzylidene)ruthenium (II), (1,3-bis(2,6-diisopropylphenyl)imidazolidin-2-ylidene)diiodo(2-((1-(methoxy(methyl)amino)-1-oxopropan-2-yl)oxy)b enzylidene)ruthenium (II), (1,3-dimesitylimidazolidin-2-ylidene)dichloro(2-iopropoxy-5-nitrobenzylidene)ruthenium(II), Dichloro[1,3-bis(2,4,6-trimethylphenyl)-2-imidazolidinylidene](2-isopropoxyphenylmethylene)ruthenium(II), Benzylidene-bis(tricyclohexylphosphine)dichlororuthenium, Dichloro[1,3-bis(2,4,6sopropylphenyl)-2-imidazolidinylidene](2-isopropoxyphenylmethylene)ruthenium(II), [1,3-Bis(2,6-di-i-propylphenyl)imidazolidin-2-ylidene](2-i-propoxy-5-nitrobenzylidene)ruthenium (II) diiodide, 1,3-Bis(2,6-di-i-propylphenyl)imidazolidin-2-ylidene)(2-i-propoxy-5- nitrobenzylidene) ruthenium(II)dichloride, (1,3-Dimesityl-imidazolidin-2-ylidene)diiodo(2-isopropoxy-5-nitrobenzylidene)ruthenium(II), Bis(1-(2,6-diethylphenyl)-3,5,5-trimethyl-3-phenylpyrrolidin-2-ylidene)(3-phenyl-1H-inden-1-ylidene)ruthenium(II) dichloride, (1-(2,6-diethylphenyl)-3,5,5-trimethyl-3-phenylpyrrolidin-2-ylidene)dichloro(2-isopropoxy-5-nitrobenzylidene) ruthenium(II), (1-(2,6-diethylphenyl)-3,5,5-trimethyl-3-phenylpyrrolidin-2-ylidene)diiodo(2-isopropoxy-5-nitrobenzylidene)ruthenium(II), Dichloro[1,3-bis(2-methylphenyl)-2-imidazolidinylidene](2-isopropoxyphenylmethylene)ruthenium(II), 1,3-Bis(2,4,6-trimethylphenyl)-4,5-dihydroimidazol-2-ylidene[2-(i-propoxy)-5-(N,N-dimethylaminosulfonyl)phenyl] methyleneruthenium(II) dichloride (resin supported), Dichloro[1,3-bis(2,4,6-trimethylphenyl)-2-imidazolidinylidene](3-phenyl-1H-inden-1-ylidene)(tricyclohexylphosphine)ruthenium(II), [1,3-Bis(2,4,6-trimethylphenyl)-2-imidazolidinylidene]-[2-[[(4-methylphenyl)imino] methyl]-4-nitrophenolyl]-[3-phenyl-1H-inden-1-ylidene] ruthenium(II)chloride, Dichloro[1,3-bis(2,4,6-trimethylphenyl)-2-imidazolidinylidene][[5-[(dimethylamino)sulfonyl]-2-(1-methylethoxy-O)phenyl] methylene-C]ruthenium(II), Dichloro[1-(2,6-diisopropylphenyl)-2,2,4-trimethyl-4-phenyl-5-pyrrolidinylidene](2-isopropoxyphenylmethylene) ruthenium(II), [1,3-Bis(2,6-trifluoroacetamido)benzylidene] ruthenium(II), Dichloro[1,3-bis(2,6-diisopropylphenyl)-2-imidazolidinylidene](benzylidene)(tricyclohexylphosphine) ruthenium(II), Dichloro[1-(2,4,6-trimethylphenyl)-2,2,4-trimethyl-4-phenyl-5-pyrrolidinylidene](2-isopropoxyphenylmethylene)ruthenium (II), Dichloro[1-(2,6-diisopropylphenyl)-2,2,4-trimethyl-4-phenyl-5-pyrrolidinylidene](2isopropoxyphenylmethylene)ruthenium (II), Dichloro[1,3-bis(2,6-diisopropylphenyl)-2-imidazolidinylidene][(2-isopropoxy)(5-pentafluorobenzoylamino)benzylidene]ruthenium(II), Dichloro[1,3-bis(2,4,6-trimethylphenyl)-2-imidazolidinylidene]{[5-(2-ethoxy-2-oxoethanamido)]-2-isopropoxybenzylidene}ruthenium (II), Dichloro[1,3-bis(2,4,6-trimethylphenyl)-2-imidazolidinylidene][(2-isopropoxy)(5-pentafluorobenzoylamino)benzylidene] ruthenium(II), (1,3-Bis(2,6-diisopropylphenyl) imidazolidin-2-ylidene)dichloro(2-((1-(methoxy(methyl) amino)-3-methyl-1-oxobutan-2-yl)oxy)benzylidene) ruthenium(II), Dichloro[1,3-bis(2,4,6-trimethylphenyl)-2-imidazolidinylidene](3-phenyl-1H-inden-1-ylidene) (pyridyl)ruthenium (II), Dichloro[1,3-bis(2,4,6-trimethylphenyl)-2-imidazolidinylidene][(2-isopropoxy)(5-trifluoroacetamido)benzylidene]ruthenium(II), Dichloro[1,3-bis(2,6-diisopropylphenyl)imidazolidin-2-ylidene][(5-isobutoxycarbonylamino)-(2-isopropoxy)benzylidene] ruthenium(II) and Dichloro[1,3-bis(2,6-diisopropylphenyl)-2-imidazolidinylidene](3-phenyl-1H-inden-1-ylidene) (triphenylphosphine)ruthenium(II).

10. The process according to claim 1, further comprising the steps of converting compound of formula (I) to compound of formula (IV)

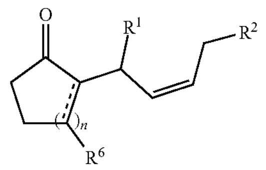

(IV)

wherein $R^1$, $R^2$ and n have the same meaning as defined in claim 1, the dotted line represents a carbon-carbon single bond or carbon-carbon double bond and $R^6$ represents a hydrogen atom, a $C_{1-3}$ alkyl group optionally substituted by a $COOR^a$ group wherein $R^a$ is a $C_{1-3}$ alkyl group.

11. The process according to claim 1, wherein n is 1;

$R^1$ is a hydrogen atom;

$R^2$ represents a methyl or an ethyl group; and

X is selected from a halogen atom, a OR group wherein R' represents a hydrogen atom, an acetyl group, a methoxymethyl group, a ethoxymethyl group, 1-butoxyethyl group, a 1-ethoxyethyl group or a trimethylsilyl group; and $R^3$, $R^4$ and $R^5$ represent a hydrogen atom.

12. The process according to claim 11, wherein X is a halogen atom.

13. The process according to claim 11, wherein the metathesis catalyst is a Ruthenium-based catalyst.

14. The process according to claim 11, further comprising the steps of converting compound of formula (I) to compound of formula (IV)

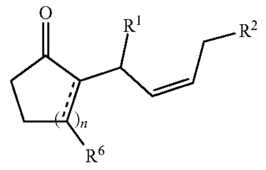

(IV)

wherein in the compound of formula (IV), n is an integer between 1 and 4, $R^1$ and $R^2$, independently from each other, represent a hydrogen atom or a $C_{1-3}$ alkyl group, the dotted line represents a carbon-carbon single bond or carbon-carbon double bond and $R^6$ represents a hydrogen atom, a $C_{1-3}$ alkyl group optionally substituted by a $COOR^a$ group wherein $R^a$ is a $C_{1-3}$ alkyl group.

* * * * *